US 6,235,769 B1

(12) United States Patent
Clary

(10) Patent No.: US 6,235,769 B1
(45) Date of Patent: May 22, 2001

(54) METHODS OF PREVENTING AND TREATING NEUROLOGICAL DISORDERS WITH COMPOUNDS THAT MODULATE THE FUNCTION OF THE C-RET RECEPTOR PROTEIN TYROSINE KINASE

(75) Inventor: Douglas Clary, San Francisco, CA (US)

(73) Assignee: Sugen, Inc., Redwood City, CA (US)

( * ) Notice: Subject to any disclaimer, the term of this patent is extended or adjusted under 35 U.S.C. 154(b) by 0 days.

(21) Appl. No.: 09/109,883

(22) Filed: Jul. 2, 1998

Related U.S. Application Data

(60) Provisional application No. 60/051,715, filed on Jul. 3, 1997.

(51) Int. Cl.[7] .................................................. A61K 31/40

(52) U.S. Cl. ........................................... 514/419; 514/418

(58) Field of Search ...................................... 514/418, 419

(56) References Cited

U.S. PATENT DOCUMENTS

| | | | |
|---|---|---|---|
| Re. 36,256 | 7/1999 | Spada et al. | 514/249 |
| 4,376,110 | 3/1983 | David | 436/513 |
| 5,217,999 | 6/1993 | Levitzki et al. | 514/613 |
| 5,302,606 | 4/1994 | Spada et al. | 514/357 |
| 5,330,992 | 7/1994 | Eissenstat et al. | 514/312 |
| 5,610,173 | 3/1997 | Schwartz et al. | 514/378 |
| 5,880,141 * | 3/1999 | Tang et al. | 514/339 |

FOREIGN PATENT DOCUMENTS

| | | |
|---|---|---|
| 0 566 226 | 10/1993 | (EP) . |
| 91/15495 | 10/1991 | (WO) . |
| 92/20642 | 11/1992 | (WO) . |
| 92/21660 | 12/1992 | (WO) . |
| 94/03427 | 2/1994 | (WO) . |
| 94/14808 | 7/1994 | (WO) . |
| 96/18738 | 6/1996 | (WO) . |
| 96/22976 | 8/1996 | (WO) . |
| 98/38984 | 9/1998 | (WO) . |
| 98/45708 | 10/1998 | (WO) . |
| 99/10325 | 9/1999 | (WO) . |

OTHER PUBLICATIONS

Andrews et al. (American Veterinary Medicine Association Panel on Euthanasia), "1993 Report of the AVMA Panel on Euthanasia," *J. American Veterinary Medicine Assocation* 202(2):229–249 (1993).

Barbacid et al., "The trk family of tyrosine protein kinase receptors," *Biochimica et Biophysica Acta* 1072:115–127 (1991).

Braunger et al., "Intracellular signaling of the Ufo/Axl receptor tyrosine kinase is mediated mainly by a multi–substrate docking–site,"*Oncogene* 14:2619–2631 (1997).

Clary et al., "TrkA Cross–linking Mimics Neuronal Responses to Nerve Growth Factor," *Molec. Bio.of the Cell* 5:549–563 (1994).

Curiel et al., "Adenovirus Enhancement of Transferrin–Polylysine–Mediated Gene Delivery," *Proc. Natl. Acad. Sci. USA* 88:8850–8854 (Oct., 1991).

Durbec et al., "GDNF Signalling Through the Ret Receptor Tyrosine Kinase," *Nature* 381:789–793 (1996).

Fendly et al., "Characterization of Murine Monoclonal Antibodies Reactive to Either the Human Epidermal Growth Factor Receptor of HER2/neu Gene Product," *Cancer Research* 50:1550–1558 (1990).

*FDA Inactive Ingredient Guide* issued by the Division of Drug Informaiton Resources (1990–1996).

Fingl and Woodbury, "Chapter 1—General Principles," in *The Pharmacological Basis of Therapeutics* 5th edition, Goodman and Gilman editors, MacMillan Publishing Co., Inc., New York, pp. 1–46 (1975).

Graham et al., "Characteristics of a Human Cell Line Transformed by DNA from Human Adenovirus Type 5," *J. of Gen. Virology* 36:59–72 (1977).

Greene et al., "PC12 Pheochromocytoma Cells: Culture, Nerve Growth Factor Treatment, and Experimental Exploitation," *Methods in Enzymology* 147:207–216 (1987).

Hawrot and Patterson, "Long–Term Culture of Dissociated Sympathetic Neurons," in *Methods in Enzymology—Cell Culture*, Jakoby and Pastan eds., Academic Press, New York, New York (1979), pp. 574–584.

Jing et al., "GDNF–Induced Activation of the Ret Protein Tyrosine Kinase Is Mediated by GDNFR– , a Novel Receptor for GDNF,"*Cell* 85:1113–1124 (1996).

Klein et al., "Disruption of the neurotrophin–3 receptor gene trkC eliminates Ia muscle afferents and results in abnormal movements," *Nature* 368:249–251 (1994).

Köhler and Milstein, "Continuous cultures of fused cells secreting antibody of predefined specificity," *Nature* 256:495–497 (1975).

Lefcort et al., "Inhibition of the NT–3 Receptor TrkC, Early in Chick Embryogenesis, Results in Severe Reductions in Multiple Neuronal Subpopulations in the Dorsal Root Ganglia," *Neuroscience* 16:3704–3713 (1996).

Massague, "Crossing Receptor Boundaries," *Nature* 382:29–30 (1996).

*The Merck Manual of Diagnosis and Therapy*, 16th edition, edited by Berkow et al, Merck Research Laboratories (1992) (Table of Contents Only).

*Mosby's Medical Nursing and Allied Health Dictionary*, 4th edition, edited by Anderson et al., Mosby, St. Louis (1994) (Table of Contents Only).

McCloskey et al., "Activation of the Axl Receptor Tyrosine Kinase Induces Mitogenesis and Transformation in 32D Cells," *Cell Growth & Differentation* 5:1105–1117 (1994).

(List continued on next page.)

Primary Examiner—Theodore J. Criares
(74) Attorney, Agent, or Firm—Foley & Lardner

(57) ABSTRACT

The invention relates in part to a method of preventing or treating an abnormal condition caused by an aberration in the function of the C-RET receptor, and specifically to the treatment and prevention of neurodegenerative disorders by administering a pharmaceutical composition that modulates the function of the C-RET receptor.

14 Claims, No Drawings

OTHER PUBLICATIONS

Moore et al., "Renal and neuronal abnormalities in mice lacking GDNF," *Nature* 382:76–79 (1996).

Obermeier et al., "Identification of Trk Binding Sites for SHC and Phosphatidylinositol 3'–Kinase and Formation of a Multimeric Signaling Complex," *J. Biol. Chem.* 268(31):22963–22966 (1993).

Obermeier et al., "Tyrosine 785 is a major determinant of Trk–substrate interaction," *The EMBO Journal* 12(3):933–941 (1993).

Pichel et al., "Defects in enteric innervation and kidney development in mice lacking GDNF," *Nature* 382:73–76 (1996).

Sachs et al., "Motogenic and Morphogenic Activity of Epithelial Receptor Tyrosine Kinases," *J. Cell Biology* 133:1095–1107 (1996).

Sambrook et al., *Molecualr Cloning: A Laboratory Manual, 2nd Edition*, Cold Spring Harbor Laboratory Press (1989) (Table of Contents—All Three Volumes) (also referred to as Maniatis).

Sanchez et al., "Renal agenesis and the absence of enteric neurons in mice lacking GDNF," *Nature* 382:70–73 (1992).

Santoro et al., "An Epidermal Growth Factor Receptor/ret Chimera Generates Mitogenic and Transforming Signals: Evidence for a ret–Specific Signaling Pathway," *Molecular and Celullar Biology* 14:663–675 (1994).

Schaack et al., "Efficient Selection of Recombinant Adenoviruses by Vectors That Express Galactosidase," *J. of Virology* 69:3920–3923 (1995).

Smeyne et al., "Severe sensory and sympathetic neuropathies in mice carrying a disrupted Trk/NGF receptor gene," *Nature* 368:246–248 (1994).

Spaargaren et al., "Antibody–induced Dimerization Activates the Epidermal Growth Factor Receptor Tyrosine Kinase," *J. Biol. Chem.* 266:1733–1739 (1991).

Treanor et al., "Characterization of a multicomponent receptor for GNDF," *Nature* 382:80–83 (1996).

Trupp et al., "Functional receptor for GDNF encoded by the c–ret proto–oncogene," *Nature* 381:785–789 (Jun. 27, 1996).

*The United States Pharmacopeia The National Formulary*, United States Pharmacopeial Convention, Rockville, MD (Jan. 1, 1990).

* cited by examiner

US 6,235,769 B1

METHODS OF PREVENTING AND TREATING NEUROLOGICAL DISORDERS WITH COMPOUNDS THAT MODULATE THE FUNCTION OF THE C-RET RECEPTOR PROTEIN TYROSINE KINASE

RELATED APPLICATIONS

This application claims priority to U.S. Provisional Patent Application Ser. No. 60/051,715, filed Jul. 3, 1997, entitled "Methods of preventing and treating neurological disorders with compounds that modulate the function of the c-ret receptor protein tyrosine kinase" by Douglas Clary and to an International Application PCT/US98/06842, now WO/98/45708, filed Apr. 7, 1998, entitled "Study and Treatment of Diseases Related to Specific Cellular Functions of Receptor Protein Tyrosine Kinases" by Douglas Clary, which claims priority to U.S. Patent Application Ser. No. 60/043,207, filed Apr. 8, 1997 entitled "Methods of Evaluating Specific Cellular Functions of Receptor Protein Tyrosine Kinases in a Ligand Independent Manner" (Lyon & Lyon Docket No. 222/299 all of which are hereby incorporated by reference herein in their entirety, including any drawings or figures.

FIELD OF THE INVENTION

The invention described herein relates to methods of preventing or treating disorders in patients suffering from the effects of neuronal degeneration. The invention is based in part on the discovery that activation of the c-ret receptor is necessary for neuronal cell survival.

BACKGROUND OF THE INVENTION

The following description of the background of the invention is provided to aid in understanding the invention, but is not admitted to be or to describe prior art to the invention.

Cellular signal transduction is a fundamental mechanism whereby extracellular stimuli are relayed to the interior of cells. One of the key biochemical mechanisms of signal transduction involves the reversible phosphorylation of proteins. Phosphorylation of amino acids regulates the activity of mature proteins by altering their structure and function.

Phosphate most often resides on the hydroxyl moiety of serine, threonine, or tyrosine amino acids in proteins. Enzymes that mediate phosphorylation of cellular effectors fall into two classes. While protein phosphatases hydrolyze phosphate moieties from phosphoryl protein substrates, protein kinases transfer a phosphate moiety from adenosine triphosphate to protein substrates. The converse functions of protein kinases and protein phosphatases balance and regulate the flow of signals in signal transduction processes.

Protein kinases are divided further into two groups: receptor and non-receptor type proteins. Receptor protein kinases comprise an extracellular region, a transmembrane region, and an intracellular region. Part of the intracellular regions of receptor protein kinases harbor a catalytic domain.

Receptor protein kinases are also divided into three classes based upon the amino acids they act upon. Some phosphorylate serine or threonine only, some phosphorylate tyrosine only, and some phosphorylate serine, threonine, and tyrosine.

Receptor protein tyrosine kinases (RPTKs) are typically activated in the cell when a ligand binds to the extracellular region of the receptor. A model for ligand mediated activation of RPTKs features the ligand bringing the receptors within close proximity to one another. Some ligands are dimers and thereby bring the receptors that bind them into close proximity with one another. By bringing two RPTKs together, ligands place RPTK intracellular catalytic regions in close proximity to one another such that they cross-phosphorylate. Cross phosphorylation requires not only the dimerization process but also the occurrence of a conformational change preceding phosphorylation. The necessity of the conformational change preceding phosphorylation is illustrated by the fact that some RPTKs, such as the insulin receptor, are pre-dimerized and inactive before binding their activating ligands.

The presence of phosphate moieties on the RPTK intracellular regions constitutes a cellular signal that causes other signal transduction molecules to bind to the RPTK. In this manner, RPTKs propagate the extracellular signal to the cell nucleus, thereby generating messages encoding proteins that cause cellular effects.

Because RPTKs control a variety of cellular function, any alteration in the normal function of an RPTK can result in an abnormal condition in an organism. For example, differentiation and survival of neuronal cells is dependent upon the proper function of RPTKs. Specifically, it has been shown that the interaction between activated Trk (Barbacid et al., *Biochimica et Biophysica Acta*, 1072:115–127, 1991) and a signaling component such as SHC is important for promoting neuronal cell differentiation and survival. Transgenic mice containing knockout mutations in genes encoding each of the known Trk receptors or the Trk ligand displayed severe neurological dysfunction and, in all cases, important types of neural tissue were absent. Smeyne et al., 1994, *Nature* 368: 246–249; Klein et al., 1994, *Nature* 268: 249–251, 1994.

Specific neurotrophic factors (generally referred to as ligands herein) have also been shown to promote neuronal survival. In particular, glial-derived neurotrophic factor (GDNF) has been identified as a neuronal survival factor. Jing et al., 1996, *Cell* 85:1113–1124; Trupp et al., 1996, *Nature* 381:785–789; Durbec et al., 1996, *Nature* 381: 789–793. GDNF has been shown to bind to a complex of C-RET and another cell surface protein GDNFR-α, which has no intracellular domain.

In an effort to discover novel treatments for diseases, biomedical researchers have designed, synthesized, and tested molecules that modulate protein kinase function in cells. Some organic molecules have been identified as modulators of RPTK function. For example, bis monocyclic, bicyclic, or heterocyclic aryl compounds (PCT WO 92/20642), vinylene-azaindole derivatives (PCT WO 94/14808), 1-cyclopropyl-4-pyridylquinolones (U.S. Pat. No. 5,330,992), styryl compounds (U.S. Pat. No. 5,217,999), styryl-substituted pyridyl compounds (U.S. Pat. No. 5,302,606), certain quinazoline derivatives (EP Application No. 0 566 266 Al), seleoindoles and selenides (PCT WO 94/03427), tricyclic polyhydroxylic compounds (PCT WO 92/21660), and benzylphosphonic acid compounds (PCT WO 91/15495) have been identified as compounds which modulate the function of protein kinases.

There remains a great need in the medical field for identifying compounds that modulate the function of RPTKs regulating neuronal survival, in particular. Many patients suffer from diseases caused by neuronal degeneration, such as Alzheimer's disease, Parkinson's disease, and amyotrophic lateral sclerosis, for example. Although neurotrophic factors have been proposed as therapeutic agents for neuronal diseases, they often cannot reach their target receptors since they rapidly degrade in the blood stream and cannot pass through cell membranes or the blood brain barrier. Thus, identifying effective therapeutics for treating neuronal diseases lies in identifying non-peptide compounds which do not rapidly degrade in the blood stream and which can pass through cell membranes and the blood-brain barrier.

SUMMARY OF THE INVENTION

The invention relates in part to methods of preventing or treating disorders in patients suffering from the effects of neuronal degradation by administering compounds that modulate the function of C-RET to a patient afflicted with such a disorder. In addition, the invention relates to pharmaceutical compositions of compounds that modulate the function of C-RET.

In a first aspect, the invention relates to a method of preventing or treating an abnormal condition in a mammal, where the abnormal condition is caused by an aberration in cell survival. The method comprises the step of administering a pharmaceutical composition comprising one or more compounds to the mammal, where the one or more compounds are modulators of C-RET RPTK.

The term "preventing" refers to decreasing the probability that an organism contracts or develops an abnormal condition.

The term "treating" refers to having a therapeutic effect and at least partially alleviating or abrogating an abnormal condition in the organism.

The term "therapeutic effect" can refer to the inhibition of cell death causing or contributing to a neuronal disorder. The term "therapeutic effect" can also refer to the inhibition or activation factors causing or contributing to the abnormal condition. A therapeutic effect relieves to some extent one or more of the symptoms of the abnormal condition. In reference to the treatment of a neuronal disorders, a therapeutic effect refers to one or more of the following: (a) an increase in the proliferation, growth, and/or differentiation of neuronal cells; (b) inhibition (i.e., slowing or stopping) of neuronal cell death; (c) inhibition of neuronal degeneration; (d) relieving to some extent one or more of the symptoms associated with the abnormal condition; and (e) enhancing the function of the affected neuronal population (e.g., increase in neurotransmitter synthesis). Compounds demonstrating efficacy against neuronal disorders can be identified as described herein.

The term "abnormal condition" refers to a function in the cells or tissues of an organism that deviates from their normal functions in that organism. An abnormal condition can relate to cell proliferation, cell differentiation, or cell survival.

Abnormal cell proliferative conditions include cancers such as fibrotic and mesangial disorders, abnormal angiogenesis and vasculogenesis, wound healing, psoriasis, diabetes mellitus, and inflammation.

Abnormal differentiation conditions include, but are not limited to neurodegenerative disorders, slow wound healing rates, and slow tissue grafting healing rates.

Abnormal cell survival conditions relate to conditions in which programmed cell death (apoptosis) pathways are activated or abrogated. A number of protein kinases are associated with the apoptosis pathways. One RPTK associated with cell survival is C-RET. Aberrations in the function of any one of the protein kinases could lead to cell immortality or premature cell death.

The term "aberration", in conjunction with the function of an RPTK in a signal transduction process, refers to a RPTK that is over- or under-expressed in an organism, mutated such that its catalytic activity is lower or higher than wild-type protein kinase activity, mutated such that it can no longer interact with a natural binding partner, is no longer modified by another protein kinase or protein phosphatase, or no longer interacts with a natural binding partner.

The term "administering" relates to a method of incorporating a compound into cells or tissues of an organism. The abnormal condition can be prevented or treated when the cells or tissues of the organism exist within the organism or outside of the organism. Cells existing outside the organism can be maintained or grown in cell culture dishes. For cells harbored within the organism, many techniques exist in the art to administer compounds, including (but not limited to) oral, parenteral, dermal, injection, and aerosol applications. For cells outside of the organism, multiple techniques exist in the art to administer the compounds, including (but not limited to) cell microinjection techniques, transformation techniques, and carrier techniques.

The abnormal condition can also be prevented or treated by administering a compound to a group of cells having an aberration in a signal transduction pathway to an organism. The effect of administering a compound on organism function can then be monitored. The organism is preferably a frog, more preferably a mouse, rat, rabbit, guinea pig, or goat, and most preferably a monkey or ape.

The term "compound" includes, but is not limited to, both antibodies and test compounds of the invention. "Compound" refers to a peptide of less than twenty, preferably less than fifteen, preferably less than ten, or most preferably less than eight amino acids in length. The term "compound" preferably refers to a peptidomimetic, more preferably refers to a non-peptide organic molecule, and most preferably refers to a non-peptide synthetic organic molecule. Examples of compounds are included in the Description of the Invention and in the Examples, herein.

The term "peptidomimetic" refers to an organic molecule with a structure related to a natural peptide, and which can exhibit or block the biological activities of the natural peptide.

The term "pharmaceutical composition" refers to a mixture of one or more compounds with other chemical components, such as diluents or carriers. The pharmaceutical composition facilitates administering the compound to an organism. Multiple techniques of administering a compound exist in the art including, but not limited to, oral, injection, aerosol, parenteral, and topical administration. Pharmaceutical compositions can also be obtained by reacting compounds with organic or inorganic acids such as hydrochloric acid, hydrobromic acid, sulfuric acid, nitric acid, phosphoric acid, methane sulfonic acid, ethane sulfonic acid, p-toluene sulfonic acid, salicylic acid and the like.

The term "composition" further refers to a mixture of indolinone compounds of the invention with other chemical components or excipients, such as solvents, diluents or carriers. The pharmaceutical composition facilitates administration of the compound to an organism.

Formulations for indolinone compounds are described in U.S. application Ser. No. 08/702,232, filed Aug. 23, 1996 and in the corresponding International patent publication WO 96/22976. Specific examples of parenteral and oral formulations for lipophilic compounds are contained in U.S. Pat. No. 5,610,173, issued Mar. 11, 1997, entitled "Formulations for Lipophilic Compounds" by D. Schwartz, et al. and U.S. patent application Ser. No. 09/034,374, filed Mar.

4, 1998, entitled "Formulations for Hydrophobic Pharmaceutical Compositions" by N. Shenoy, et al. (Lyon & Lyon Docket No. 231/299) and PCT Application No. PCT/US98/04134, filed Mar. 4, 1998, entitled "Formulations for Hydrophobic Pharmaceutical Compositions" by N. Shenoy, et al., which are hereby included herein by reference in their entirety, including any drawings, figures, and tables.

The term "pharmaceutically acceptable" or "pharmaceutical" as used herein refers to solutions or components of the pharmaceutical composition that do not prevent the therapeutic compound from exerting a therapeutic effect and do not cause unacceptable adverse side effects. Examples of pharmaceutically acceptable reagents are provided in *The United States Pharmacopeia The National Formulary*, United States Pharmacopeial Convention, Inc., Rockville, Md. 1990 and *FDA Inactive Ingredient Guide* 1990, 1996 issued by the Division of Drug Information Resources (both are hereby incorporated by reference herein, including any drawings).

Unacceptable side effects vary for different diseases. Generally, the more severe the disease the more toxic effects which will be tolerated. Unacceptable side effects for different diseases are known in the art.

The term "physiologically acceptable" defines a carrier or diluent that does not cause significant irritation to an organism and preferably does not abrogate the biological activity and properties of the compound.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Many salts dissolved in buffered solutions are utilized as diluents in the art. One commonly used buffered solution is phosphate buffered saline because it mimics the salt conditions of human blood. Because buffer salts can control the pH of a solution at low concentrations, a diluent rarely modifies the biological activity of a compound.

The term "C-RET" as used herein refers to a particular RPTK which is described more fully in the Detailed Description of the Invention. C-RET is a proto-oncogene RPTK that phosphorylates protein targets on tyrosine residues that has been shown to be activated by glial-derived neurotrophic factor (GDNF) in cells (Jing et al., 1996, Cell 85:1113–1124; Trupp, et al., 1996, Nature 381:789–793).

The term "RPTK" is used herein to describe a protein with an extracellular region that binds a ligand, a transmembrane region, and an intracellular region. RPTKs phosphorylate proteins on tyrosine residues. The nucleic acid sequence encoding an RPTK of the invention can be isolated from eukaryotic organisms.

The term "extracellular region" refers to a polypeptide portion of a RPTK of the invention that exists outside the cell membrane. A requirement of the extracellular region of chimeras of the invention is that it has specific binding affinity to another molecule, preferably an antibody of the invention. The extracellular region of the chimeras must not bind to any other protein on the cell surface and not normally be expressed on the surface of the specific cell type used in the invention.

The term "antibody" refers to an antibody (e.g., a monoclonal or polyclonal antibody), or antibody fragment, having specific binding affinity to RPTK's or fragments thereof, preferably the extracellular region of the RPTK's.

By "specific binding affinity" is meant that the antibody binds to target (RPTK) polypeptides with greater affinity than it binds to other polypeptides under specified conditions. Antibodies having specific binding affinity to a RPTK may be used in methods for detecting the presence and/or amount of a protein RPTK in a sample by contacting the sample with the antibody under conditions such that an immunocomplex forms and detecting the presence and/or amount of the antibody conjugated to the RPTK. Diagnostic kits for performing such methods may be constructed to include a first container containing the antibody and a second container having a conjugate of a binding partner of the antibody and a label, such as, for example, a radioisotope. The diagnostic kit may also include notification of an FDA approved use and instructions therefor.

The term "polyclonal" refers to antibodies that are heterogenous populations of antibody molecules derived from the sera of animals immunized with an antigen or an antigenic functional derivative thereof, preferably an extracellular region of a RPTK. For the production of polyclonal antibodies, various host animals may be immunized by injection with the antigen. Various adjuvants may be used to increase the immunological response, depending on the host species. "Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art. See, for example, Kohler, et al., *Nature* 256:495–497 (1975), and U.S. Pat. No. 4,376,110.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the polypeptide target.

The term "ligand" as used herein refers to a polypeptide molecule which binds to the extracellular region of a receptor. Examples of ligands include, but are not limited to, nerve growth factor (NGF), which binds to the extracellular region of the TRK receptor, and GDNF which binds to a complex of C-RET and GDNFR-α.

The term "transmembrane region" as used herein refers to the region of a polypeptide that connects the extracellular region to the intracellular region, preferably in a chimera of the invention. The transmembrane region can be isolated from any transmembrane protein and is preferably from the same polypeptide source as the intracellular region. Transmembrane regions are often rich in hydrophobic amino acids, such as phenylalanine, tyrosine, tryptophan, valine, leucine, and isoleucine, which interact with fatty acid moieties of the membrane lipids and thereby anchor the chimera to the cell membrane.

The term "intracellular region" of an RPTK defines any region existing on the inner side of the cell. An intracellular region of a protein of the invention preferably includes the region of an RPTK with catalytic activity, and no other region of the RPTK.

DNA recombinant techniques known in the art provide the means of connecting an RPTK intracellular region to the extracellular region of another RPTK via a transmembrane region. In addition, the intracellular region of an RPTK can be attached to the extracellular region of a protein other than an RPTK, such as a receptor protein phosphatase.

The term "catalytic activity", in the context of the invention, defines the rate at which an RPTK intracellular region phosphorylates a substrate. Catalytic activity can be measured, for example, by determining the amount of a substrate converted to a phosphorylated product as a function of time. Catalytic activity can be measured by methods of the invention by holding time constant and determining the concentration of a phosphorylated substrate after a fixed period of time. Phosphorylation of a substrate occurs at the active-site of a protein kinase. The active-site is normally a cavity in which the substrate binds to the protein kinase and is phosphorylated.

The term "organism" relates to any living being comprised of at least one cell. An organism can be as simple as one eukaryotic cell or as complex as a mammal.

The term "eukaryote" refers to an organism comprised of cells that contain a nucleus. Eukaryotes are differentiated from "prokaryotes" which do not house their genomic DNA inside a nucleus. Prokaryotes include unicellular organisms such as bacteria, while eukaryotes are represented by, for example, yeast, invertebrates, and vertebrates.

The term "mammal" refers preferably to such organisms as mice, rats, rabbits, guinea pigs, sheep, and goats, more preferably to cats, dogs, monkeys, and apes, and most preferably to humans.

In other preferred embodiments of methods of preventing or treating an abnormal condition in a mammal, the method at least partially reduces the symptoms associated with the abnormal condition, which is preferably caused by an aberration in cell survival.

The term "aberration in cell survival" as used herein refers to a condition in which cell survival is enhanced or decreased with respect to cell survival parameters in normal cells. Cell survival can be shortened in such disorders as Parkinson's disease, Alzheimer's disease, and amyotrophic lateral sclerosis. Cell survival can be increased in cancer related conditions.

Alzheimer's disease manifests itself as pre-senile dementia. The disease is characterized by confusion, memory failure, disorientation, restlessness, speech disturbances, and hallucination in mammals (Medical, Nursing, and Allied Health Dictionary, 4th Ed., 1994, Editors: Anderson, Anderson, Glanze, St. Louis, Mosby).

Parkinson's disease is a slowly progressive, degenerative, neurologic disorder characterized by resting tremor, loss of postural reflexes, and muscle rigidity and weakness (Medical, Nursing, and Allied Health Dictionary, 4th Ed., 1994, Editors: Anderson, Anderson, Glanze, St. Louis, Mosby).

Amyotrophic lateral sclerosis is a degenerative disease of the motor neurons characterized by weakness and atrophy of the muscles of the hands, forearms, and legs, spreading to involve most of the body and face (Medical, Nursing, and Allied Health Dictionary, 4th Ed., 1994, Editors: Anderson, Anderson, Glanze, St. Louis, Mosby).

In preferred embodiments of methods of preventing or treating an abnormal condition in a mammal, the abnormal condition is a neurodegenerative disorder, preferably selected from the group consisting of Alzheimer's disease, Parkinson's disease, amyotrophic lateral sclerosis. Preferred methods at least partially prevent or reduce a symptom associated with the abnormal condition.

The term "neurodegenerative disorder" as used herein refers to an abnormality in a mammal in which neuronal integrity is threatened. Neuronal integrity can be threatened when neuronal cells display decreased survival or when the neurons can no longer propagate a signal.

In another preferred embodiment, the invention relates to the method of treating or preventing an abnormal condition in the mammal, where the mammal is identified as having said abnormal condition. Mammals can be identified as having, for example, a neurological disorder such as Alzheimer's disease, Parkinson's disease, or amyotrophic lateral sclerosis by monitoring the symptoms manifested in the mammals afflicted with these disorders. These symptoms are well documented in publications known to those skilled in the art.

In other preferred embodiments of the method of treating or preventing an abnormal condition in a mammal, the one or more compounds are identified by a method comprising: (a) expressing said C-RET in cells; (b) contacting said cells with one or more compounds; and (c) monitoring an effect on said cells. Preferably, the effect is a change or an absence of a change in cell phenotype, which includes, but is not limited to: apoptosis and cell proliferation; catalytic activity of C-RET; and the interaction between C-RET and a natural binding partner.

The term "expressing" refers to the functional presence of C-RET in a cell. This can be achieved by many methods well-known in the art, to include transfection of a nucleic acid vector encoding C-RET and any other sequences necessary for expression including a promoter, for example. Appropriate, but not limiting methods include those described in the Examples, herein.

The term "transfecting" defines a number of methods to insert a nucleic acid vector or other nucleic acid molecules into a cellular organism. These methods involve a variety of techniques, such as treating the cells with high concentrations of salt, an electric field, detergent, or DMSO to render the outer membrane or wall of the cells permeable to nucleic acid molecules of interest or use of various viral transduction strategies.

The term "nucleic acid vector" relates to a single or double stranded circular nucleic acid molecule that can be transfected into cells and replicated within or independently of a cell genome. A circular double stranded nucleic acid molecule can be cut and thereby linearized upon treatment with restriction enzymes. An assortment of nucleic acid vectors, restriction enzymes, and the knowledge of the nucleotide sequences cut by restriction enzymes are readily available to those skilled in the art. A nucleic acid molecule encoding a chimeric receptor can be inserted into a vector by cutting the vector with restriction enzymes and ligating the two pieces together.

The term "contacting" as used herein refers to mixing a solution comprising one or more test compounds with a liquid medium bathing the cells of the methods. The solution comprising the one or more test compounds may also comprise another component, such as dimethylsulfoxide (DMSO), which facilitates the uptake of the one or more test compounds into the cells of the methods. The solution comprising the test compounds may be added to the medium bathing the cells by utilizing a delivery apparatus, such as a pipet-based device or syringe-based device. "Test compound" includes, but is not limited to, both antibodies and compounds of the invention.

The term "modulates" refers to the ability of a test compound (or "modulator") to alter the function of a RPTK. A modulator preferably activates or inhibits the activity of a RPTK. A modulator can enhance or inhibit the catalytic activity of the RPTK by binding to the RPTK. By binding to the RPTK, the compound may inhibit the catalytic activity of the RPTK by blocking interactions between the RPTK and a substrate that it phosphorylates. A compound may activate the RPTK by bringing RPTKs into close proximity with one another such that they cross phosphorylate and thereby activate more effectively, or by increasing the probability that a catalysis-dependent conformational change occurs in the RPTK.

In addition, a modulator can inhibit the interaction between a RPTK and a natural binding partner by blocking interactions between amino acids at the interface of the complex. In addition, a modulator may inhibit the activity of a natural binding partner which acts upon the RPTK. Alternatively, a modulator can enhance the interaction between a RPTK and a natural binding partner by forming additional favorable interactions between the two molecules at the complex interface. A modulator preferably inhibits the catalytic activity of a protein kinase, or more preferably activates the catalytic activity of a protein kinase.

The term "activates" refers to increasing the cellular function of a RPTK. The RPTK function is preferably the interaction with a natural binding partner or catalytic activity. An activator of C-RET is a cellular factor that is responsible for the cellular response of C-RET after it binds to GDNF. C-RET activators include, but are not limited to GRB2 and SOS. Compounds can enhance the interaction between C-RET and GRB2 or SOS and effectively activate the cellular function of C-RET.

The term "inhibit" refers to decreasing the cellular function of a RPTK. The RPTK function is preferably the interaction with a natural binding partner or catalytic activity. A hypothetical example of a protein that decreases the function of the RPTK, C-RET, is a protein phosphatase that dephosphorylates the activated receptor and thereby decreases C-RET's ability to recruit other proteins necessary for the C-RET activation response, such as GRB2 and SOS.

The term "signal transduction pathway" refers to the molecules that propagate an extracellular signal through the cell membrane to become an intracellular signal. This signal can then stimulate a cellular response. The polypeptide molecules involved in signal transduction processes are typically receptor and non-receptor protein tyrosine kinases, receptor and non-receptor protein phosphatases, SRC homology 2 and 3 domains, phosphotyrosine binding proteins (SRC homology 2 (SH2) and phosphotyrosine binding (PTB and PH) domain containing proteins), proline-rich binding proteins (SH3 domain containing proteins), nucleotide exchange factors, and transcription factors.

The term "substrate" as used herein refers to a molecule phosphorylated by a RPTK. RPTKs phosphorylate substrates on tyrosine amino acids.

The term "effect" preferably describes a change or an absence of a change in cell phenotype. "Effect" can also describe a change or an absence of a change in the catalytic activity of the RPTK. "Effect" can also describe a change or an absence of a change in an interaction between the RPTK and a natural binding partner.

The term "cell phenotype" refers to the outward appearance of a cell or tissue or the function of the cell or tissue. Examples of cell phenotype include, but are not limited to, cell size (reduction or enlargement), cell shape, cell proliferation (increased or decreased numbers of cells), cell differentiation (changes in physiological state), cell survival, apoptosis (cell death), or the utilization of a metabolic nutrient (e.g., glucose uptake). Changes or the absence of changes in cell phenotype are readily measured by techniques known in the art.

The term "cell proliferation" refers to the rate at which a group of cells divides. The number of cells growing in a vessel can be quantified by a person skilled in the art when that person visually counts the number of cells in a defined area using a common light microscope. Alternatively, cell proliferation rates can be quantified by laboratory apparatae that optically measure the density of cells in an appropriate medium.

Cell differentiation and survival are phenomena simply measured by methods in the art. These methods can involve observing the number of cells or the appearance of cells under a microscope with respect to time (days).

The term "apoptosis" as used herein refers to programmed cell death. It has been shown by example herein that activation of C-RET can prolong cell survival and decrease the probability of cell death.

The term "interaction", in the context of the invention, describes a complex formed between a RPTK and a natural binding partner or compound, preferably between a RPTK intracellular region and a natural binding partner or compound.

The term "complex" refers to an assembly of at least two molecules bound to one another. Signal transduction complexes often contain at least two protein molecules bound to one another. For instance, a protein tyrosine receptor protein kinase, GRB2, SOS, RAF, and RAS assemble to form a signal transduction complex in response to a mitogenic ligand.

The term "natural binding partner" refers to polypeptides that bind to a RPTK. Natural binding partners can play a role in propagating a signal in a protein kinase signal transduction process. A change in the interaction between a RPTK and a natural binding partner can manifest itself as an increased or decreased probability that the interaction forms, or an increased or decreased concentration of the RPTK/natural binding partner complex.

A RPTK natural binding partner can bind to a RPTK intracellular region with high affinity. High affinity represents an equilibrium binding constant on the order of $10^{-6}$ M or less. In addition, a natural binding partner can also transiently interact with a RPTK intracellular region and chemically modify it. Protein kinase natural binding partners are chosen from a group consisting of, but not limited to, SRC homology 2 (SH2) or 3 (SH3) domains, other phosphoryl tyrosine binding (PTB) domains, guanine nucleotide exchange factors, protein phosphatases, and other protein kinases. Methods of determining changes in interactions between protein kinases and their natural binding partners are readily available in the art.

In other preferred embodiments, the invention relates to the method of treating or preventing an abnormal condition in a mammal, where one or more compounds in the pharmaceutical composition are indolinone compounds of Formula I:

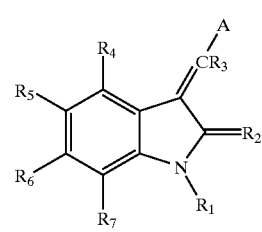

(I)

where, $R_1$ is hydrogen or alkyl; $R_2$ is oxygen or sulfur; $R_3$ is hydrogen; $R_4$, $R_5$, $R_6$, and $R_7$ are each independently selected from the group consisting of hydrogen, alkyl, alkoxy, aryl, aryloxy, alkaryl, alkaryloxy, halogen, trihalomethyl, S(O)R, SO₂NRR', SO₃R, SR, NO₂, NRR', OH, CN, C(O)R, OC(O)R, NHC(O)R, (CH₂)ₙCO₂R, CONRR', and (CH₂)ₙONRR'; A is a five-membered heteroaryl ring selected from the group consisting of thiophene, pyrrole, pyrazole, imidazole, 1,2,3-triazole, 1,2,4-triazole, oxazole, isoxazole, thiazole, isothiazole, 2-sulfonylfuran, 4-alkylfuran, 1,2,3-oxadiazole, 1,2,4-oxadiazole, 1,2,5-oxadiazole, 1,3,4-oxadiazole, 1,2,3,4,-oxatriazole, 1,2,3,5-oxatriazole, 1,2,3-thiadiazole, 1,2,4-thiadiazole, 1,2,5-thiadiazole, 1,3,4-thiadaizole, 1,2,3,4-thiatriazole, 1,2,3,5-thiatriazole, and tetrazole, wherein said five-membered ring is optionally substituted at one or more positions with one or more substituents independently selected from the group consisting of alkyl, alkoxy, aryl, aryloxy, alkaryl, alkaryloxy, halogen, trihalomethyl, S(O)R, SO₂NRR', SO₃R, SR, NO₂, NRR', OH, CN, C(O)R, OC(O)R, NHC(O)R, (CH₂)ₙCO₂R, CONRR', and (CH₂)ₙONRR'; n is 0–3; R is selected from the group consisting of hydrogen, alkyl, and aryl; and R' is selected from the group consisting of hydrogen, alkyl, and aryl, wherein said alkyl is optionally substituted with a six-membered heteroaliphatic ring, and wherein said six-membered ring is optionally substituted at one or more positions with substituents selected from the group consisting of alkyl, alkoxy, halogen, trihalomethyl, NO₂, and (CH₂)ₙCO₂R.

In highly preferred embodiments, A is selected from the group consisting of thiophene and pyrrole, where the thiophene and pyrrole are optionally substituted with one or more substituents selected from the group consisting of alkyl, alkoxy, aryl, aryloxy, alkaryl, alkaryloxy, halogen, trihalomethyl, S(O)R, SO₂NRR', SO₃R, SR, NO₂, NRR', OH CN, C(O)R, OC(O)R, NHC(O)R, (CH₂)ₙCO₂R, CONRR', and (CH₂)ₙONRR; n is 0–3; R is selected from the group consisting of hydrogen, alkyl, and aryl; and R' is selected from the group consisting of hydrogen, alkyl, and aryl, wherein said alkyl is optionally substituted with a six-membered heteroaliphatic ring, and where the six-membered ring is optionally substituted at one or more positions with substituents selected from the group consisting of alkyl, alkoxy, halogen, trihalomethyl, NO₂, and (CH₂)ₙCO₂R.

In preferred embodiments, the indolinone compounds of formula I able to modulate the activity of C-RET are identified in a method comprising: expressing C-RET in cells; contacting the cells with one or more of the indolinone compounds; and monitoring an effect on the cells, as described previously.

The term "indolinone" is used as that term is commonly understood in the art, and includes a large subclass of substituted or unsubstituted compounds that are capable of being synthesized from an aldehyde moiety and an oxindole moiety.

The term "oxindole" refers to an oxindole compound substituted with chemical substituents. Oxindole compounds are of the general structure:

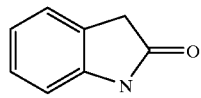

The term "substituted" refers to compounds of the invention that are derivatized with any number of chemical substituents, typically by replacing one or more of the hydrogen atoms present in the compound's general structure.

The term "compound" further refers to the compound or a pharmaceutically acceptable salt, ester, amide, prodrug, isomer, or metabolite, thereof.

The term "pharmaceutically acceptable salt" refers to a formulation of a compound that does not abrogate the biological activity and properties of the compound.

Pharmaceutical salts can be obtained by reacting a compound of the invention with inorganic or organic acids such as hydrochloric acid, hydrobromic acid, sulfuric acid, nitric acid, phosphoric acid, methane sulfonic acid, ethane sulfonic acid, p-toluene sulfonic acid, salicylic acid and the like. Also specifically envisioned are salts of free acids.

The term "ester" refers to a chemical moiety with formula —(R)ₙ—COOR', where R and R' are independently selected from the group consisting of saturated or unsaturated alkyl and homocyclic or heterocyclic ring moieties and where n is 0 or 1.

The term "amide" refers to a chemical substituent of formula —NHCOR, where R is selected from the group consisting of hydrogen, alkyl, hydroxyl, and homocyclic or heterocyclic ring moieties, where the ring is optionally substituted with one or more substituents independently selected from the group consisting of alkyl, halogen, trihalomethyl, carboxylate, nitro, or ester.

The term "prodrug" refers to an agent that is converted into the parent drug in vivo. Prodrugs may be easier to administer than the parent drug in some situations. For example, the prodrug may be bioavailable by oral administration but the parent is not, or the prodrug may improve solubility to allow for intravenous administration.

The term "saturated alkyl" refers to an alkyl moiety that does not contain any alkene or alkyne moieties. The alkyl moiety may be branched or non-branched.

The term "unsaturated alkyl" refers to an alkyl moiety that contains at least one alkene or alkyne moiety. The alkyl moiety may be branched or non-branched.

The term "aromatic" refers to an aromatic group which has at least one ring having a conjugated pi electron system and includes both carbocyclic aryl (e.g. phenyl) and heterocyclic aryl groups (e.g. pyridine).

The term "carbocyclic" refers to a compound which contains one or more covalently closed ring structures, and in which the atoms forming the backbone of the ring are all carbon atoms. The term thus distinguishes carbocyclic from heterocyclic rings in which the ring backbone contains at least one atom which is different from carbon. The term "heteroaromatic" refers to an aromatic group which contains at least one heterocyclic ring.

The term "aliphatic ring" refers to a compound which contains one or more covalently closed ring structures, and in which at least one of the atoms forming the backbone is a saturated carbon atom (e.g. cyclohexane). The term "heteroaliphatic ring" refers to a ring system in which at least one of the atoms forming the backbone is a heteroatom (e.g. tetrahydropyran).

The term "amine" refers to a chemical moiety of formula NR₁R₂ where R₁ and R₂ are independently selected from the group consisting of hydrogen, saturated or unsaturated alkyl, and five-membered or six-membered aryl or heteroaryl ring moieties, where the ring is optionally substituted with one or more substituents independently selected from the group consisting of alkyl, halogen, trihalomethyl, carboxylate, nitro, and ester moieties.

The term "halogen" refers to an atom selected from the group consisting of fluorine, chlorine, bromine, and iodine. The term "trihalomethyl" refers to the —CX₃ group, where X is a halogen.

The term "ketone" refers to a chemical moiety with formula —(R)$_n$—CO—R', where R and R' are selected from the group consisting of saturated or unsaturated alkyl and five-membered or six-membered aryl or heteroaryl moieties and where n is 0 or 1. The term "carboxylic acid" refers to a chemical moiety with formula —(R)$_n$—COOH, where R is selected from the group consisting of saturated or unsaturated alkyl and five-membered or six-membered aryl or heteroaryl moieties and where n is 0 or 1.

The term "alcohol" refers to a chemical substituent of formula —ROH, where R is selected from the group consisting of hydrogen, saturated or unsaturated alkyl, and five-membered or six-membered aryl or heteroaryl ring moieties, where the ring is optionally substituted with one or more substituents independently selected from the group consisting of alkyl, halogen, trihalomethyl, carboxylate, nitro, and ester moieties.

The term "alkoxyalkyl moiety" refers to a chemical substituent of formula —(R)$_n$—OR', where R' is an optionally substituted saturated or unsaturated alkyl moiety or an optionally substituted ring and n is 0 or 1, and where R' is an optionally substituted alkyl or optionally substituted aromatic, heteroaromatic, aliphatic, or heteroaliphatic ring moieties. When n is 0, then the alkoxyalkyl moiety is called an "alkoxy moiety".

The term "aldehyde" refers to a chemical moiety with formula —(R)$_n$—CHO, where R is selected from the group consisting of saturated or unsaturated alkyl and five-membered or six-membered aryl or heteroaryl moieties and where n is 0 or 1.

The term "sulfone" refers to a chemical moiety with formula —SO$_2$—R, where R is selected from the group consisting of saturated or unsaturated alkyl and five-membered or six-membered aryl or heteroaryl moieties.

The term "thiol" refers to a chemical moiety with formula —(R)$_n$—SH, where R is selected from the group consisting of optionally substituted alkyl or optionally substituted aromatic, heteroaromatic, aliphatic, or heteroaliphatic ring moieties and where n is 0 or 1. The term "thioether" refers to a chemical moiety of the formula —(R)$_n$—SR' where both R and R' are selected from the group consisting of optionally substituted alkyl or optionally substituted aromatic, heteroaromatic, aliphatic, or heteroaliphatic ring moieties and where n is 0 or 1.

The term "acyl" refers to chemical moieties of the general formula —C(O)R. When R is hydrogen the molecule containing the acyl group is an aldehyde. When R is an alkyl, an aliphatic ring, or an aromatic ring, then the molecule containing the acyl group is a ketone.

In another preferred embodiment of methods of treating or preventing an abnormal condition in a mammal, the one or more compounds are of formula II:

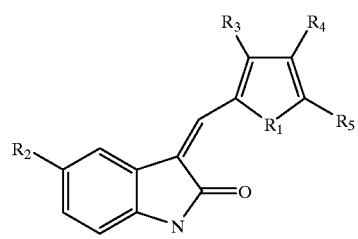

(II)

where R$_1$ is independently selected from the group consisting of nitrogen and sulfur; R$_2$ is (CH$_2$)$_n$CO$_2$, where n is selected from the group consisting of 0, 1, and 2; and R$_3$, R$_4$, and R$_5$ are independently selected from the group consisting of hydrogen and a branched or unbranched saturated alkyl consisting of 1, 2, or 3 carbons.

In another preferred embodiment of methods of treating or preventing an abnormal condition in a mammal, the one or more compounds are selected from the group consisting of Compound I, Compound II, Compound III, Compound IV, Compound V, and Compound VI.

By Compound I is meant an indolinone compound with the following structure:

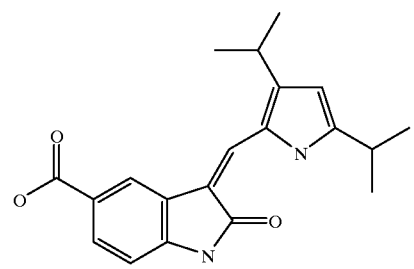

By Compound II is meant an indolinone compound with the following structure:

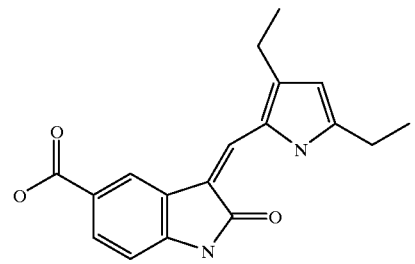

By Compound III is meant an indolinone compound with the following structure:

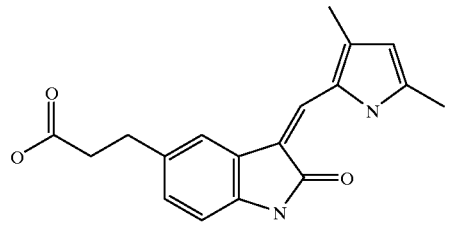

By Compound IV is meant an indolinone compound with the following structure:

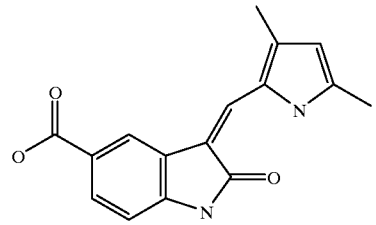

By Compound V is meant an indolinone compound with the following structure:

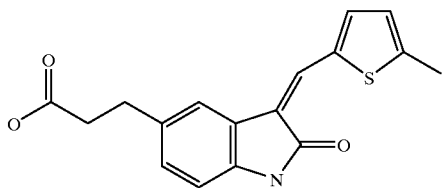

By Compound VI is meant an indolinone compound with the following structure:

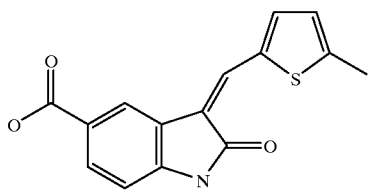

In other preferred embodiments of methods of treating or preventing an abnormal condition in a mammal, the pharmaceutical composition is comprised of one or more compounds that are non-peptide molecules and one or more physiologically acceptable solvents, diluents, or carriers in a formulation. Preferably, the formulation is oral, topical, or parenteral. Preferably these compounds act intracellularly and can traverse the blood-brain barrier. Preferably the compounds activate the catalytic activity of the RPTK, inactivate an inhibitor of the RPTK, or activate an activator of the RPTK. Most preferably, the RPTK is C-RET.

The term "non-peptide molecule" refers to a compound that is not a polymer of amino acids. A non-peptide molecule preferably does not contain chemical moieties that hydrolyze in physiological conditions, e.g. a peptidomimetic.

The term "solvent" as used herein refers to a chemical compound that facilitates the solubilization of compounds of the invention. Examples of solvents include, but are not limited to, pharmaceutically acceptable alcohols, such as ethanol and benzyl alcohol; polyoxyhydrocarbyl compounds, such as poly(ethylene glycol); pharmaceutically acceptable surfactants such as CREMOPHOOR EL; polyglycolized lipids, such as GELUCIRE and LABRASOL; and pharmaceutically acceptable oils, such as miglyol 812.

The term "pharmaceutically acceptable alcohol" as used herein refers to alcohols which are liquids at about room temperature (approximately 20° C.). These include propylene glycol, ethanol, 2-(2-ethoxyethoxy)ethanol (TRANSCUTOL®, Gattefosse, Westwood, N.J. 07675), benzyl alcohol, and glycerol.

The term "polyoxyhydrocarbyl compound" as used herein refers to a water soluble carbohydrate such as glucose, sucrose, maltotriose, and the like; water soluble carbohydrate derivatives such as gluconic acid and mannitol, and oligosaccharides; and water soluble polymers such as polyvinylpyrrolidone, poly(vinyl alcohol), and in particular, polyethers such as other polyoxyalkylenes including poly (ethylene glycol) or other water soluble mixed oxyalkylene polymers and the polymeric form of ethylene glycol. Although polyoxyhydrocarbyl compounds preferably contain more than one carbon, oxygen, and hydrogen atom, some molecules such as poly(ethylene imine) are also included.

A particularly preferred class of solubilizing polyoxyhydrocarbyl moieties comprises poly(ethylene glycol) (PEG) and PEG derivatives, such as PEG monomethyl ether. Other suitable PEG derivatives include PEG-silicon derived ethers. Many of these polymers are commercially available in a variety of molecular weights. Others may be conveniently prepared from commercially available materials, such as by coupling of amino-PEG moiety to a haloalkyl silyl or silane moiety.

Suitable PEGs may vary in molecular weight from about 200 g/mol to about 20,000 g/mol or more, more preferably 200 g/mol to 5,000 g/mol, even more preferably 250 g/mol to 1,000 g/mol, and most preferably 250 g/mol to 500 g/mol. The choice of a particular molecular weight may depend on the particular indolinone-based compound chosen and its molecular weight and degree of hydrophobicity, as well as the particular application for which the formulation is to be used.

The term "pharmaceutically acceptable surfactantu as used herein refers to a compound that can solubilize compounds of the invention into aqueous solutions. Preferably for parenteral formulations, the surfactant is a non-ionic surfactant. Examples of pharmaceutically acceptable surfactants include POLYSORBATE 80® and other polyoxyethylene sorbitan fatty acid esters, glyceryl monooleate, polyvinyl alcohol, ethylene oxide copolymers such as PLURONIC™ (a polyether) and TETRONIC™ (BASF), polyol moieties, and sorbitan esters. Preferably ethoxylated castor oils, such as CREMOPHOR ELO, are used for the formulation of indolinone-based compounds.

The term "ethoxylated castor oil" as used herein refers to castor oil that is modified with at least one oxygen containing moiety. In particular the term refers to castor oil comprising at least one ethoxyl moiety.

Further, the term "pharmaceutically acceptable surfactant" as used herein in reference to oral formulations, includes pharmaceutically acceptable non-ionic surfactants (for example polyoxyethylenepolypropylene glycol, such as POLOXAMER® 68 (BASF Corp.) or a mono fatty acid ester of polyoxyethylene (20) sorbitan monooleate (TWEEN® 80), polyoxyethylene (20) sorbitan monostearate (TWEEN® 60), polyoxyethylene (20) sorbitan monopalmitate (TWEEN® 40), polyoxyethylene (20) sorbitan monolaurate (TWEEN® 20) and the like); polyoxyethylene castor oil derivatives (for example, polyoxyethyleneglycerol-triricinoleate or polyoxyl 35 castor oil (CREMOPHOR® EL, BASF Corp.), polyoxyethyleneglycerol oxystearate (CREMOPHOR RH 40 (polyethyleneglycol 40 hydrogenated castor oil) or CREMOPHOR® RH 60 (polyethyleneglycol 60 hydrogenated castor oil), BASF Corp.) and the like); or a pharmaceutically acceptable anionic surfactant.

The term "polyglycolized lipids" as used herein refers to mixtures of monoglycerides, diglycerides, or triglycerides and polyethyleneglycol monoesters and diesters formed by the partial alcoholysis of vegetable oil using PEG of 200 g/mol to 2,000 g/mol or by the esterification of fatty acids using PEG 200 g/mol to 2,000 g/mol and glycerols. Preferably these include GELUCIRE® 35/10, GELUCIRE® 44/14, GELUCIRE® 46/07, GELUCIRE® 50/13, GELUCIRE® 53/10, and LABRASOL®.

The term "pharmaceutically acceptable oils" as used herein refers to oils such as mineral oil or vegetable oil (including safflower oil, peanut oil, and olive oil), fractionated coconut oil, propylene glycol monolaurate, mixed triglycerides with caprylic acid and capric acid, and the like. Preferred embodiments of the invention feature mineral oil, vegetable oil, fractionated coconut oil, mixed triglycerides with caprylic acid, and capric acid. A highly preferred embodiment of the invention features Miglyol 812 (available from Huls America, USA).

The term "acts intracellularly" as used herein refers to a compound that can modulate the function of a RPTK by binding to the intracellular region of the RPTK. In addition, the compound can bind to a natural binding partner of the RPTK intracellular region.

The "blood-brain" barrier is an anatomic feature of the brain that is thought to comprise walls of capillaries in the central nervous system combined with surrounding glial membranes (Medical, Nursing, and Allied Health Dictionary, 4th Ed., 1994, Editors: Anderson, Anderson, Glanze, St. Louis, Mosby).

A second aspect of the invention features a pharmaceutical composition comprising one or more compounds selected from the group consisting of Compound I, Compound II, Compound III, Compound IV, Compound V, and Compound VI, and one or more physiologically acceptable solvents or diluents or carriers in a formulation. Preferably, the formulation is oral, topical, or parenteral. The one or more compounds of the pharmaceutical composition can modulate a RPTK cellular function, either by activating or inhibiting a RPTK cellular function, and most preferably activate C-RET.

A final aspect of the invention features a pharmaceutical composition that modulates the function of the C-RET receptor, comprising one or more compounds identified by a method comprising: (a) expressing said C-RET in cells; (b) contacting said cells with one or more compounds; and (c) monitoring an effect on said cells; and one or more physiologically acceptable solvents in a formulation. Preferably, the formulation is oral, topical, or parenteral.

The summary of the invention described above is not limiting and other features and advantages of the invention will be apparent from the following detailed description of the invention, and from the claims.

DETAILED DESCRIPTION OF THE INVENTION

The invention relates in part to methods of preventing or treating disorders in patients suffering from the effects of neuronal degradation by administering pharmaceutical compositions comprised of compounds that modulate the function of C-RET to patients afflicted with such a disorder.

RPTKs are essential regulatory molecules controlling a variety of cellular functions. For this reason, any alteration in the function of a RPTK can result in an abnormal condition in an organism. Just one of the many functions controlled by RPTKs is cell survival. Aberrations in cell survival can lead to neurological disorders.

The methods of preventing or treating disorders in patients suffering from the effects of neuronal degradation are based in part on the discovery that activation of the C-RET receptor is necessary for neuronal cell survival. The C-RET receptor has been implicated in neuronal survival by methods that activate the receptor in a ligand independent fashion. These methods utilize antibodies specific for the Trk extracellular region of a Trk extracellular region/C-RET intracellular region chimeric receptor. The antibodies specifically activate the chimeric receptor by bringing the C-RET intracellular regions in close proximity such that they cross phosphorylate and thereby activate. These methods were utilized to discover the function of C-RET before the ligand that activates this receptor, GDNF, was known to those skilled in the art.

Identifying effective therapeutics for treating neuronal diseases lies in identifying non-peptide compounds that activate C-RET. Non-peptide compounds are preferred since they are often stable in a patient's blood stream. In addition, non-peptide compounds can be selected such that they can pass through cell membranes and the blood-brain barrier. Although many of the non-peptide molecules discovered to modulate the function of RPTKs only inhibit their targets, activating compounds of RPTKs are being discovered.

I. Neurological Disorders and Signal Transduction

Abnormalities in signal transduction pathways can lead to various diseases through both underactivity and over activity of the RPTKs involved in these pathways. Examples of disorders which are characterized by underactivity of a RPTK in a signal transduction pathway include various neurodegenerative diseases such as myasthenia gravis, amyotrophic lateral sclerosis, cervical spondylosis, and Alzheimer's disease. A neurological disease possibly characterized by overactivity of an RPTK in a signal transduction pathway is neurofibromatosis. See, generally, The Merck Manual of Diagnosis and Therapy, 16th Edition, 1992.

The development and maintenance of cellular communication networks within the central and peripheral nervous system is regulated by neurotrophic factors, which through activation of specific cell surface receptors generate differentiation and survival signals in neuronal cell types. Binding of the neurotrophic factor to its receptor initiates a cellular signal transduction cascade involving diverse cytoplasmic components which eventually results in a specific nuclear response. Specific cellular responses in nerve cells can include, for example, neurite outgrowth, acquisition of Na+-based action potential and cell survival in serum-free medium.

The complex processes involved in cell survival are mediated by diverse and divergent signal transduction pathways. The multiple phosphorylated tyrosines found in activated RPTKs serve as binding sites for different signaling components, which in turn modulate the transduction of a signal along a particular pathway. In the case of the NGF receptor Trk, it has been shown that specific phosphorylated tyrosines within the cytoplasmic portion of the receptor can bind to the signaling components phospholipase C-gamma (PLC-gamma), SHC and the non-catalytic subunit of phosphatidylinositol-3'-kinase, p85. Obermeier, A., *EMBO Journal* 12:933–941, 1993 and Obermeier, A., *J. Biol. Chem.* 268:22963–22966, 1993. These proteins in turn each stimulate different and distinct further downstream signaling components until instructions are finally transmitted to the cell nucleus. For example, SHC has been shown to bind to the Grb2/SOS complex, which in turn allows the activation of ras. Activation of PLC-gamma, on the other hand, leads to the generation of phosphatidylinositol metabolites, such as inositol 1,4,5-triphosphate, which cause the release of calcium ions from intracellular compartments and the generation of diacylglycerol, the natural activator of PKC.

Until recently, it was not yet understood which RPTKs were responsible for regulating cell survival. Methods of the invention, described herein, demonstrated that the C-RET receptor regulates neuronal cell survival.

II. Method of Determining the Function of C-RET

The following method was used to demonstrate that the C-RET receptor regulates neuronal survival. This method specifically activates RPTKs in cells in a ligand-independent fashion. The RPTKs are activated with antibodies specific to the extracellular region of a chimeric receptor. The chimeric receptor can contain an extracellular region and an intracellular region from two different RPTKs. Specifically, a chimera can contain the extracellular region of the Trk receptor and an intracellular region of C-RET. Activation of such a chimeric construct resulted in the prolonged survival of various neuronal cells. Examples of such studies are provided herein.

A chimera, as used in the context of the invention, defines a polypeptide constructed from polypeptides of at least two different proteins. The chimeric polypeptides are encoded by nucleic acid molecules harbored by a nucleic acid vector transfected into cells. Hence, a chimera can contain the extracellular and transmembrane region from one type of RPTK and the intracellular region from another type of RPTK.

The chimeric feature of the method provides versatility as the intracellular region of virtually any known RPTK can be incorporated readily into a chimeric construct using DNA recombinant techniques existing in the art. The chimeras comprise a polypeptide extracellular region, a transmembrane region, and an intracellular region of a RPTK. The chimeric polypeptides are encoded by nucleic acid molecules harbored by a nucleic acid vector transfected into cells or tissues. The extracellular region of the chimera is a polypeptide region that exists outside of the cell and specifically binds to an antibody of the method. The intracellular region of the chimera exists inside the cell and comprises any part of a RPTK intracellular region.

The chimeric feature of the method also confers specificity as chimeras can be activated in a specific manner by an antibody having specific binding affinity to the polypeptide extracellular region. An antibody can specifically bind to a single type of extracellular region of a chimera on cell surfaces. As antibodies are Y-shaped" molecules that can bind two polypeptide molecules, antibodies can bring the chimeras in close proximity to one another in the cell. Once the intracellular regions of the chimera are in close proximity to one another, they can cross phosphorylate one another and become activated. The effect of a compound on the cellular function of a RPTK can then be measured by monitoring changes in cell phenotype, catalytic activity of the RPTK, or interactions of the RPTK with natural binding partners. Hence, antibody-induced activation of chimeras specifically activates RPTK intracellular regions without causing other cellular effects.

To achieve specific activation of chimeric receptor constructs, the method features a cross species chimera/cell system. In this system, the extracellular region of the chimeric receptor is selected from an organism distantly related to the organism from which the cells expressing the chimeric receptor are derived. This cross species strategy ensures that endogenous receptors expressed on the cell surface are not activated by the antibodies raised against the extracellular region of the chimeric construct. For example, the antibodies of the invention have specific binding affinity for the trk extracellular region from chicken. The antibodies having specific binding affinity for the chicken trk extracellular region will consequently not cross react with the endogenous trk receptor of rat or human cells when the chimeric constructs are expressed in the se cells. Thus, the antibodies of the invention prevent cross reactivity with endogenous receptors expressed on the surface of mammalian cells since the antibodies have specific binding affinity to a distinct trk receptor of a different type of organism.

III. Function of C-RET in Cells

Using the method described above, it was determined that C-RET regulates cell survival. Signal transduction molecules that form a complex with C-RET as a result of these phosphoryl moieties, such as GRB2, SOS, ras, and raf, propagate a signal in the cell that promotes neural survival. Thus, compounds that promote the interactions of the se stimulatory molecules of C-RET would enhance the activity of C-RET. Alternatively, protein phosphatases can remove the phosphoryl moieties placed on the intracellular region of C-RET in response to GDNF, and thus inhibit the signaling capability C-RET. Thus, compounds that inhibit phosphatases of C-RET will probably enhance the signaling capacity of C-RET.

C-ret is implicated in the development and survival of enteric, synaptic, and sensory neurons and neurons of the renal system upon stimulation by GDNF (Jing, et al., 1996, Cell 85:1113–1124; Trupp, et al., 1996, Nature 381:785–789; Durbec, et al., 1996, Nature 381:789–793). Lack of function mutations in C-RET can lead to Hirschsprung's disease, for example, which manifests itself as a decrease in intestinal tract innervation in mammals. Thus, compounds that activate C-RET are potential therapeutic agents for the treatment of neurodegenerative disorders, including, but not limited to, Hirschsprung's disease, Parkinson's disease, Alzheimer's disease, and amyotrophic lateral sclerosis. Compounds that inhibit C-RET function are possible anti-cancer agents as over-expression of C-RET in cells is implicated in cancers, such as cancer of the thyroid.

Modulation of C-RET activity may also be useful in treating cancers of the nerve tissue, such as neuroblastoma, even if an abnormality is not found the signaling pathway.

IV. Therapeutics for Neurological Disorders

The development of effective therapeutics for treating and preventing neurological disorders lies in identifying non-peptide compounds which do not rapidly degrade in the blood stream and which can pass through cell membranes and the blood-brain barrier. Several companies are attempting to treat neurodegenerative diseases (such as amyotrophic lateral sclerosis) by administering exogenous recombinant neurotrophic factors (such as BDNF) to mammals, in the hope that the factor will stimulate new growth and differentiation of nerve cells. Although administration of neurotrophic factors may stimulate the growth and differentiation of nerve cells grown on plates, the neurotrophic factors will likely be rapidly degraded in the blood stream by proteases since they are composed of amino acids. In addition, the neurotrophic factors cannot pass through cell membranes or the blood brain barrier. In order to treat Parkinson's disease or Alzheimer's disease, these therapeutics need to reach the brain in order to be efficacious.

For these reasons, non-peptide compounds are likely candidates as therapeutics for neurological disorders. These compounds must be selected for their ability to activate C-RET in order to treat or prevent neurological diseases. The methods set forth herein can select non-peptide molecules as activators of C-RET. In addition, select compounds are probable activators of C-RET. These compounds are set forth WO 96/40113 and its related priority documents. Examples of indolinone compounds are also set forth herein by example. These applications and publication are incorporated herein by reference in their entirety, including any figures, tables, and drawings.

V. Other Embodiments

Methods for evaluation of disorders, methods for monitoring changes in cells, methods of identifying compounds, methods of isolating compounds which interact with a RPTK, compositions of compounds that interact with a RPTK, and derivatives of complexes are disclosed in detail with respect to the protein PYK-2 in PCT publication WO 96/18738. This publication is incorporated herein by reference in its entirety, including any drawings. Those skilled in the art will appreciate that such descriptions are applicable to the present invention and can be easily adapted to it. Those skilled in the art will also appreciate that any modifications made to a complex can be manifested in a modification to any of the molecules in that complex. Thus, the invention includes any modifications to nucleic acid molecules, polypeptides, antibodies, or compounds in a complex.

In addition, the WO 96/18738 provides disclosure describing the recombinant DNA techniques pertaining to the present invention, nucleic acid vectors, the nucleic acid elements of these vectors, the types of cells that can harbor these vectors, methods of delivering these vectors to cells or tissues, methods of producing and purifying antibodies, methods of constructing hybridomas that produce these antibodies, methods of detecting signaling molecule complexes, methods of detecting interactions with natural binding partners, antibodies to complexes, disruption of RPTK protein complexes, purification and production of complexes, transgenic animals containing nucleic acid vectors encoding a RPTK, antisense and ribozyme approaches, and gene therapy techniques. Those skilled in the art will readily appreciate that such descriptions are applicable to the present invention and can be easily adapted to it.

VI. Pharmaceutical Formulations And Routes Of Administration.

The compounds described herein can be administered to a human patient per se, or in pharmaceutical compositions where it is mixed with suitable carriers or excipient(s). Techniques for formulation and administration of the compounds of the instant application may be found in "Remington's Pharmaceutical Sciences," Mack Publishing Co., Easton, Pa., latest edition.

a) Routes Of Administration.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Alternately, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

b) Composition/Formulation.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the PTK modulating compounds of the invention may be provided as salts with pharmaceutically compatible counter ions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

c) Effective Dosage.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

For any compound used in the methods of the invention, the therapeutically effective dose can be estimated initially from cell culture assays. For example, a dose can be formulated in animal models to achieve a circulating concentration range that includes the ICSO as determined in cell culture (i.e., the concentration of the test compound which achieves a half-maximal inhibition of the PTK activity). Such information can be used to more accurately determine useful doses in humans.

Toxicity and therapeutic efficacy of the compounds described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_5$ with little or no toxicity. The dosage may vary within this range depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p.1).

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g., the concentration necessary to achieve 50–90% inhibition of the kinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

d) Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

VII. Synthesis Of Indolinone Compounds

Descriptions of methods for the general synthesis of indolinone compounds are provided in U.S. application Ser. No. 08/702,282, which is incorporated herein by reference in its entirety, including any drawings and figures.

Other synthetic techniques, such as those described in International patent publication WO 96/22976, published Aug. 1, 1996 may also be used or modified by those skilled in the art to make the compounds of the present invention (hereby incorporated herein by reference in its entirety including any drawings, figures, or tables).

VIII. Administration Of Pharmaceutical Agent Formulations

Methods of determining the dosages of compounds to be administered to a patient and modes of administering compounds to an organism are disclosed in U.S. application Ser. No. 08/702,232, filed Aug. 23, 1996 and International patent publication number WO 96/22976, published Aug. 1, 1996, both of which are incorporated herein by reference in their entirety, including any drawings. Those skilled in the art will appreciate that such descriptions are applicable to the present invention and can be easily adapted to it.

The proper dosage depends on various factors such as the type of disease being treated, the particular composition being used, and the size and physiological condition of the patient. More specifically, the administered amount is the amount of compound required to effectively prevent development or alleviate symptoms of the disease or disorder in the subject being treated. Such a determination can be made by those of ordinary skill in the art in determining therapeutic dosages and is within the scope of routinely determined tasks.

Therapeutically effective doses for the compounds described herein can be estimated initially from cell culture and animal models. For example, a dose can be formulated in animal models to achieve a circulating concentration range that initially takes into account the $IC_{50}$ as determined in cell culture assays. The animal model data can be used to more accurately determine useful doses in humans. However, the final dose will be determined in clinical trials based on clinical endpoints well-known in the art.

Plasma half-life and biodistribution of the drug and metabolites in the plasma, tumors, and major organs can also be determined to facilitate the selection of drugs most appropriate to inhibit a disorder. For example, HPLC analysis can be performed on the plasma of animals treated with the drug and the location of radio-labeled compounds can be determined using detection methods such as X-ray, CAT scan, autoradiography, and MRI. Compounds that show potent inhibitory activity in the screening assays, but have poor pharmacokinetic characteristics, can be optimized by altering the chemical structure and retesting. In this regard, compounds displaying good pharmacokinetic characteristics can be used as a model.

Toxicity studies can also be carried out by measuring the blood cell composition. For example, toxicity studies can be carried out in a suitable animal test (e.g., mice in the example below) as follows: 1) the compound is administered to mice (an untreated control mouse should also be used); 2) blood samples are periodically obtained via the tail vein from one mouse in each treatment group; and 3) the samples are analyzed for red and white blood cell counts, blood cell composition, and the percent of lymphocytes versus polymorphonuclear cells. A comparison of results for each dosing regime with the controls indicates if toxicity is present.

At the termination of each toxicity study, further studies can be carried out by sacrificing the animals (preferably, in accordance with the American Veterinary Medical Association guidelines Report of the American Veterinary Medical Assoc. Panel on Euthanasia, *Journal of American Veterinary Medical Assoc.*, 202:229–249, 1993). Representative animals from each treatment group can then be examined by gross necropsy for immediate evidence of metastasis, unusual illness, or toxicity. Gross abnormalities in tissue are noted, and tissues are examined histologically. Compounds causing a reduction in body weight or blood components are less preferred, as are compounds having an adverse effect on major organs. In general, the greater the adverse effect the less preferred the compound.

For the treatment of cell proliferative disorders the expected daily dose of an indolinone compound of the invention is 1 to 1000 $mg/m^2/day$, preferably 10 to 500 $mg/m^2/day$, and most preferably 10 to 250 $mg/m^2/day$. Drugs can be delivered less frequently provided plasma levels of the active moiety are sufficient to maintain therapeutic effectiveness.

Plasma levels should reflect the potency of the drug. Generally, the more potent the compound the lower the plasma levels necessary to achieve efficacy.

Routes of administration of the compounds or pharmaceutical compositions containing compounds of the present invention may include, but are not limited to, oral, rectal, transmucosal or intestinal administration; intramuscular, subcutaneous, intramedullary injections, as well as intrathecal, direct intraventricular, intravenous, intraperitoneal, intranasal, or intraocular injections; transdermal, topical, vaginal and the like. Dosage forms include, but are not limited to, tablets, troches, dispersions, suspensions, suppositories, solutions, patches, capsules, creams, minipumps, etc. The compounds of this invention may also be administered locally via an injection or in a targeted drug delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in a form prescribed by a governmental agency regulating the manufacture, use, or sale of pharmaceuticals, which notice is reflective of approval by the agency of the form of the polynucleotide for human or veterinary administration. Such notice, for example, may be the labeling approved by the U.S. Food and Drug Administration or other governmental agencies for prescription drugs, or the approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of arthritis, endometriosis, ocular neovascularization, solid tumor growth and metastases, and excessive scarring during wound healing.

IX. Indolinone Compound Formulations

The methods of the invention include the administration of indolinone compounds to patients in formulations. Formulations for indolinone compounds are described in U.S. application Ser. No. 08/702,232, filed Aug. 23, 1996 and in International patent publication No. WO 96/22976. Some indolinone compounds are insoluble in aqueous environments, so they require the addition of compounds that can solubilize them before administration of the pharmaceutical agents to a patient. Specific formulations, methods of making and methods of use for hydrophobic indolinone compounds are described in U.S. patent Ser. No. 5,610,173, entitled "Formulations for Lipophilic Compounds" by D. Schwartz et al., U.S. patent application Ser. No. 09/034,374, entitled "Formulations for Hydrophobic Pharmaceutical Agents," filed Mar. 4, 1998 (Lyon & Lyon Docket No. 232/299), and the PCT application PCT/US98/04134, of the same title, also filed Mar. 4, 1998, all hereby incorporated by reference herein in their entirety including any drawings, figures, or tables. The components of the formulations bind to the hydrophobic regions of the pharmaceutical agents exposing the polar regions of the solubilizing components to the solvent environment. This encapsulation of the pharmaceutical agents renders them soluble in aqueous environments.

Formulations may comprise carriers, diluents, fillers, binders, and other excipient(s) at the dosage level required to treat or ameliorate the disease and/or disorder. The compounds of this invention and/or compositions thereof may be enclosed or encapsulated in an ingestible carrier in the form of a capsule, sachet, cachet, paper or other container or by a disposable container such as an ampule. A carrier or diluent may be semi-solid, solid or liquid, which serves as a vehicle, excipient, or medium for the active therapeutic substance. Diluents and carriers suitable for pharmaceutical compositions of the present invention are known to one of ordinary skill in the art.

Other methods associated with the invention are described in the Examples disclosed herein.

EXAMPLES

The examples below are not limiting and are merely representative of various aspects and features of the present invention. The examples below demonstrate Alp methods of identifying compounds that modulate the function of C-RET. In addition, the examples below demonstrate compounds that activate RPTKs. Furthermore, the examples below demonstrate methods used to identify the role of C-RET in cell survival. These methods specifically activate RPTKs in a ligand independent manner. The examples also demonstrate the specificity as well as the versatility of the methods.

Example 1
Methods of Identifying Compounds That Modulate the Function of C-RET

An enzyme linked immunosorbant assay (ELISA) can be conducted to measure the catalytic activity of C-RET and more specifically, the inhibition or activation of compounds on the catalytic activity of C-RET. The following assay can be conducted to measure catalytic activity of C-RET in PC12CTAret cells.

The PC12CTAret cells are created by techniques well known to those skilled in the art. For example, the c-ret gene may be subcloned from a nucleic acid vector described in the following examples into a nucleic acid vector suitable for stably transfecting PC12 cells. These nucleic vectors are commonly and commercially available for such purposes. The methods of cloning the genes of interest into these nucleic acid vectors and the methods of transfecting these nucleic acid constructs into cells are also well known to those skilled in the art. Sambrook, Fritsch, Maniatis, *Molecular Cloning, A Laboratory Manual 2nd Ed.*, Cold Spring Harbor Laboratory Press, 1989.

The materials and protocol for the C-RET ELISA assay are as follows:

Materials:

a. Falcon 10-cm tissue culture dishes (Falcon Cat. #3003);

b. Corning 96-well ELISA plates (Corning Cat. # 25805-96);

c. Falcon 96-well tissue culture plates (Falcon Cat. #3072);

d. NUNC 96 well V bottom polypropylene plates (Applied Scientific Catalog No. AS-72092);

e. PC12CTAret (PC12 cells expressing a chimeric form of c-ret: extracellular domain of chicken trkA and transmembrane and intracellular domains of human c-ret, with an HA epitope tag fused to carboxyl terminus);

f. Collagen I, bovine (Collaborative Biomedical, Cat. # 40231);

g. NGF (nerve growth factor). 25 $\mu$g/mL stock (prepared in: 100 mM NaCl, 50 mM sodium acetate, pH 5.3) (Austral Biologicals Cat. # GF-022);

h. dimethylsulfoxide (100%) (Sigma Catalog No. D-8418);

i. PBS, $Ca^{++}$- and $Mg^{++}$-free (Gibco Cat. # 14190-029); j. Culture medium for PC12CTAret:

RPMI (Gibco Cat. # 11875-093)
+10% horse serum, (Gibco Cat # 16050-023),
+5% fetal bovine serum (Gibco Cat # 16000-028),
+1% Penicillin-Streptomycin (Gibco Cat 15140-015),
+400 $\mu$g/mL G418 (Geneticin®; Gibco Cat # 11811-031);

k. TBST Buffer (50 mM Tris (pH 7.2), 150 mM NaCl, and 0.1% Tween-20);

l. HNTG Buffer (20 mM HEPES buffer pH 7.5, 150 mM NaCl, 0.1% Triton X-100, 10% Glycerol, 5 mM EDTA, 1 mM sodium orthovanadate, 5 mM Napyrophosphate);

m. Anti-HA monoclonal antibody, clone 12CA5 (Boehringer Mannheim Cat. # 1666606);

n. Biotinylated anti-phosphotyrosine monoclonal antibody, 4G10-Biotin.(Upstate Biotechnology Cat. # 16-103);

o. Europium-labeled Streptavidin (Wallac Cat. # 1244-360);

p. Assay buffer (Wallac Cat. # 1244-106); and q. Enhancement solution (Wallac Cat. # 1244-105);

Protocol:

1. PC12CTAret was subcloned in a PC12 cell line that expresses a chimeric HA-tagged c-ret receptor under the CMV promoter (vector pcDNA3, Invitrogen). The cells were passed when they are 60–70% confluent (about $1\times10^7$ cells/plate), usually 1:6 once every four days. Cells can be removed from the plates by pipetting medium over them several times.

2. Precoat the 96-well cell plates with collagen I. Dilute the collagen stock to 10 μg/mL with PBS $Ca^{++}$- and $Mg^{++}$-free and add 100 μL per well. Let stand at least 15 minutes, and shake out.

3. Harvest the PC12CTAret cells in 5 mL of growth medium (without G418) by pipetting up and down several times. After counting, adjust the cell suspension to have $5\times10^5$ cells/mL so that $5\times10^4$ cells are seeded by adding 100 μL per well. The plates are assayed the next day.

4. Coat Corning 96-well ELISA plates with 0.5 μg/well 12CA5 in PBS buffer (100 μl at 5 mg/mL) 2 hours at room temperature with agitation.

5. Dilute drugs to 10× concentration in RPMI or RPMI containing 10% DMSO such that each working dilution is 10% DMSO final concentration.

6. NGF is diluted to 40 ng/mL in complete PC12CTAret medium.

7. Add NGF and drugs to the cells. 13 μL of diluted NGF is added per well, followed by 13 μL of 10× concentrated drug. Shake gently and put back in $CO_2$ incubator for 90 minutes.

8. For wells to be used as positive receptor phosphorylation controls add NGF to 50 ng/mL final concentration for the last 15 minutes.

9. After the coating period with capture antibody, remove unbound antibody from the ELISA plates by inverting; rinse twice with TBST.

10. After the 90 minute incubation with drug, remove medium from cell plates by inverting, pat on paper towels to absorb excess liquid and add 100 μL HNTG* buffer. Shake vigorously for 5 min. to complete lysis.

11. Transfer lysate to coated ELISA and incubate at room temperature for 1 hour with agitation.

12. Remove lysate by inverting plates, wash twice with TBST and pat on paper towels to absorb excess liquid.

13. Add 100 μL detection antibody 4G10-Biot. at 75 ng/mL in TBST. Incubate for 60 minutes at room temperature with agitation.

14. Remove detection antibody and wash twice with TBST as in step 12.

15. Add 100 μL Eu-Steptavidin at 50 ng/mL in Assay Buffer. Incubate for 30 minutes at room temperature with agitation.

16. Remove Eu-Steptavidin and wash four times with TBST as in step 12.

17. Add 100 μL Enhancement Solution, shake for 5 minutes at room temperature.

18. Determine assay results by analyzing the plate fluorescence on Wallac DELFIA 1234 fluorometer.

Example 2

Methods of Identifying Compounds That Modulate the Function of RPTKs

An enzyme linked immunosorbant assay (ELISA) can be conducted to measure the catalytic activity of the FLK-1 receptor and more specifically, the inhibition or activation of indolinone compounds of the catalytic activity of the FLK-1 receptor. The following assay was conducted to measure catalytic activity of the FLK-1 receptor in FLK-1/NIH3T3 cells.

One skilled in the art can adapt such a procedure to other receptor tyrosine protein kinases to identify compounds that modulate the function of the receptor.

This type of assay can be developed for nearly any RPTK using well known techniques utilized by persons of ordinary skill in the art. The FLK-1/NIH3T3 cell lines are also created by techniques well known to those skilled in the art. The NIH3T3 cells were stably transfected with gene constructs containing the FLK-1 gene. The nucleic acid vectors used for this type of procedure are commonly and commercially available to those skilled in the art. The methods of cloning the genes of interest into these nucleic acid vectors and the methods of transfecting these nucleic acid constructs into cells are also well known to those skilled in the art. Sambrook, Fritsch, Maniatis, *Molecular Cloning, A Laboratory Manual 2nd Ed.*, Cold Spring Harbor Laboratory Press, 1989.

The materials and protocol for the FLK-1 ELISA assay are as follows:

Materials:

a. Corning 96-well ELISA plates (Corning Catalog No. 25805-96);

b. Cappel goat anti-rabbit IgG (catalog no. 55641);

c. PBS (Gibco Catalog No. 450-1300EB);

d. TBSW Buffer (50 mM Tris (pH 7.2), 150 mM NaCl and 0.1% Tween-20);

e. Ethanolamine stock (10% ethanolamine (pH 7.0), stored at 4° C.)

f. HNTG buffer (20 mM HEPES buffer (pH 7.5), 150 mM NaCl, 0.2% Triton X-100, and 10% glycerol);

g. EDTA (0.5 M, pH 7.0 as a 100× stock);

h. Sodium ortho vanadate (0.5 M as a 100× stock);

i. Sodium pyro phosphate (0.2 M as a 100× stock);

j. NUNC 96 well V bottom polypropylene plates (Applied Scientific Catalog No. AS-72092);

k. NIH3T3 C7#3 Cells (FLK-1 expressing cells);

l. DMEM with 1× high glucose L Glutamine (catalog No. 11965-050);

m. FBS, Gibco (catalog no. 16000-028);

n. L-glutamine, Gibco (catalog no. 25030-016);

o. VEGF, PeproTech, Inc. (catalog no. 100-20; kept as 1 μg/100 μL stock in Milli-Q $dH_2O$ and stored at −20° C.);

p. Affinity purified anti-FLK-1 antiserum;

q. Monoclonal antibody specific for phosphotyrosine (see, Fendley, et al., 1990, *Cancer Research* 50:1550–1558);

r. EIA grade Goat anti-mouse IgG-POD (BioRad catalog no. 172-1011);

s. 2,2-azino-bis(3-ethylbenz-thiazoline-6-sulfonic acid (ABTS) solution (100 mM citric acid (anhydrous), 250 mM $Na_2HPO_4$ (pH 4.0), 0.5 mg/mL ABTS (Sigma catalog no. A-1888)), solution should be stored in dark at 4° C. until ready for use;

t. $H_2O_2$ (30% solution) (Fisher catalog no. H325)

u. $ABTS/H_2O_2$ (15 mL ABTS solution, 2 μL $H_2O_2$) prepared 5 minutes before use and left at room temperature;

v. 0.2 M HCl stock in $H_2O$;

w. dimethylsulfoxide (100%)(Sigma Catalog No. D-8418); and y. Trypsin-EDTA (Gibco BRL Catalog No. 25200-049).

Protocol:

1. Coat Corning 96-well ELISA plates with 1.0 μg per well Cappel Anti-rabbit IgG antibody in 0.1 M $Na_2CO_3$ pH 9.6. Bring final volume to 150 µL per well. Coat plates overnight at 4° C. Plates can be kept up to two weeks when stored at 4° C.

2. Grow cells in Growth media (DMEM, supplemental with 2.0 mM L-Glutamine, 10% FBS) in suitable culture dishes until confluent at 37° C., 5% $CO_2$.
3. Harvest cells by trypsinization and seed in Corning 25850 polystyrene 96-well roundbottom cell plates, 25.000 cells/well in 200 µL of growth media.
4. Grow cells at least one day at 37° C., 5% $CO_2$.
5. Wash cells with D-PBS 1×.
6. Add 200 µL/well of starvation media (DMEM, 2.0 mM 1-Glutamine, 0.1% FBS). Incubate overnight at 37° C., 5% $CO_2$.
7. Dilute Compounds/Extracts 1:20 in polypropylene 96 well plates using starvation media. Dilute dimethylsulfoxide 1:20 for use in control wells.
8. Remove starvation media from 96 well cell culture plates and add 162 µL of fresh starvation media to each well.
9. Add 18 µL of 1:20 diluted Compound/Extract dilution (from step 7) to each well plus the 1:20 dimethylsulfoxide dilution to the control wells (+/−VEGF), for a final dilution of 1:200 after cell stimulation. Final dimethylsulfoxide is 0.5%. Incubate the plate at 37° C., 5% $CO_2$ for two hours.
10. Remove unbound antibody from ELISA plates by inverting plate to remove liquid. Wash 3 times with TBSW+0.5% ethanolamine, pH 7.0. Pat the plate on a paper towel to remove excess liquid and bubbles.
11. Block plates with TBSW+0.5% Ethanolamine, pH 7.0, 150 µL per well. Incubate plate thirty minutes while shaking on a microtiter plate shaker.
12. Wash plate 3 times as described in step 10.
13. Add 0.5 µg/well affinity purified anti-FLU-1 polyclonal rabbit antiserum. Bring final volume to 150 µL/well with TBSW+0.5% ethanolamine pH 7.0. Incubate plate for thirty minutes while shaking.
14. Add 180 µL starvation medium to the cells and stimulate cells with 20 µL/well 10.0 mM sodium ortho vanadate and 500 ng/mL VEGF (resulting in a final concentration of 1.0 mM sodium ortho vanadate and 50 ng/mL VEGF per well) for eight minutes at 37° C., 5% $CO_2$. Negative control wells receive only starvation medium.
15. After eight minutes, media should be removed from the cells and washed one time with 200 µL/well PBS.
16. Lyse cells in 150 µL/well HNTG while shaking at room temperature for five minutes. HNTG formulation includes sodium ortho vanadate, sodium pyro phosphate and EDTA.
17. Wash ELISA plate three times as described in step 10.
18. Transfer cell lysates from the cell plate to ELISA plate and incubate while shaking for two hours. To transfer cell lysate pipette up and down while scrapping the wells.
19. Wash plate three times as described in step 10.
20. Incubate ELISA plate with 0.02 µg/well UB40 in TBSW+05% ethanolamine. Bring final volume to 150 µL/well. Incubate while shaking for 30 minutes.
21. Wash plate three times as described in step 10.
22. Incubate ELISA plate with 1:10,000 diluted EIA grade goat anti-mouse IgG conjugated horseradish peroxidase in TBSW+0.5% ethanolamine, pH 7.0. Bring final volume to 150 µL/well. Incubate while shaking for thirty minutes.
23. Wash plate as described in step 10.
24. Add 100 µL of ABTS/$H_2O_2$ solution to well. Incubate ten minutes while shaking.
25. Add 100 µL of 0.2 M HCl for 0.1 M HCl final to stop the color development reaction. Shake 1 minute at room temperature. Remove bubbles with slow stream of air and read the ELISA plate in an ELISA plate reader.

Example 3

Potential Therapeutics For Neurological Disorders

Selected compounds are known to inhibit particular receptor protein tyrosine kinases with high affinity and specificity. For example, see U.S. patent application Ser. Nos. 08/702,282 and 08/485,323 and International Patent Publication Number WO 96/22976 for descriptions of indolinone compounds, which are incorporated herein by reference in their entirety, including any figures, tables, and drawings. Most of the indolinone compounds specified inhibit RPTKs with high affinity, but many of them do not inhibit the catalytic activity of these protein kinases.

However, the following indolinone compounds activated selected RPTKs. $EC_{200}$ values were measured for the following indolinone compounds in the FLK-1 ELISA. $EC_{200}$ values are the concentration of the indolinone compound that yielded a two-hundred percent increase in catalytic activity in the FLK-1 ELISA.

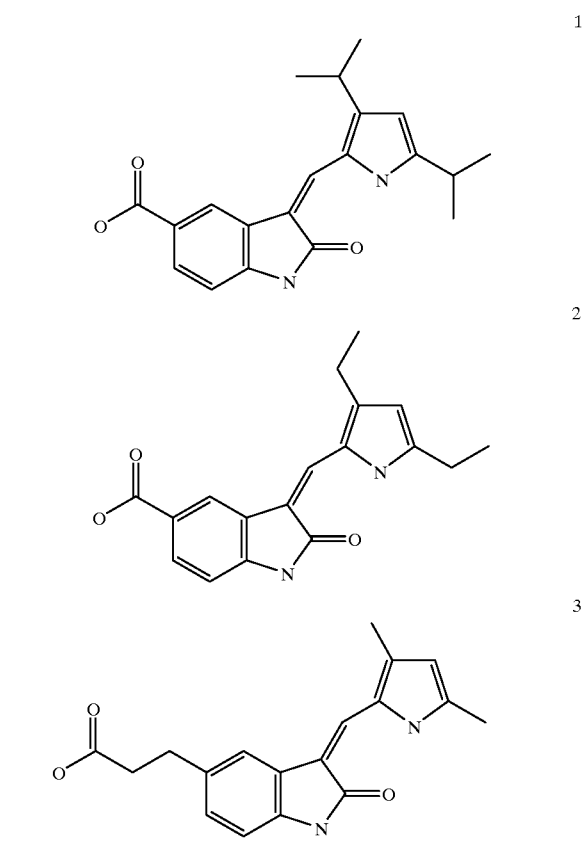

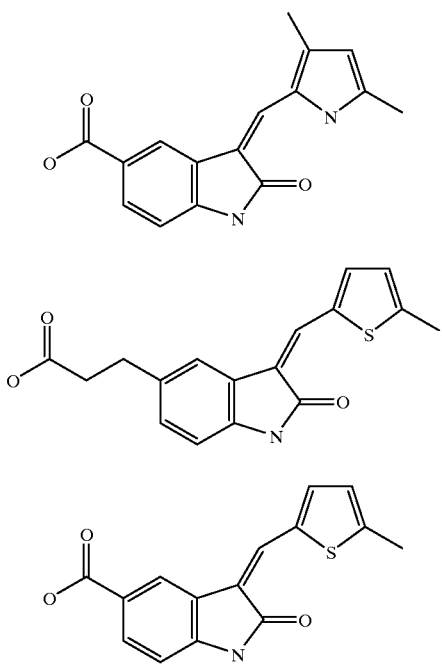

The EC$_{200}$ values for indolinones 1 through 6 are as follows:

| Indolinone | EC$_{200}$ ($\mu$M) |
|---|---|
| 1 | 10 |
| 2 | 2.8 |
| 3 | 32 |
| 4 | 2.8 |
| 5 | >100 |
| 6 | 46 |

Example 4

Specific Activation Of RPTKS By Antibodies

The following examples demonstrate that the intracellular region of a RPTK could be activated when it was fused to a trk extracellular region isolated from chicken. This chimeric construct was activated by an antibody that had specific binding affinity for the trk extracellular region from chicken organisms. In particular, the chimeric constructs were activated by polyclonal antibody preparation raised against the chicken trkA receptor. The antibody specifically activated the chimeric construct in cells, since the cells did not express any other proteins harboring regions homologous to the trk extracellular region from chicken. Thus, the antibodies distinguished between endogenous trkA receptor expressed on the surface of the rat cells, and the chimeric construct containing the chicken trkA extracellular region, also expressed on the surface of the cells.

The antibody preparation used in the experiments, called CTA, was a rabbit antibody raised against the entire extracellular domain of chicken trkA expressed in COS cells. The antibody was specific for chick trkA and did not cross-react with the rat receptor, nor did it elicit biological activities in rat cells. It did, however, strongly recognize the chick trkA receptor by immunoblot or immunoprecipitation and acted as a ligand which activated the chicken receptor. A useful control for these experiments was to activate the endogenous rat trkA receptor without influencing the introduced chimeric receptor. This specific activation was achieved through the use of the RTA IgG preparation, which recognized the rat receptor but not the chick receptor.

An assumption made in the experiments was that the chimeric receptor activated by the CTA antibody did not in turn activate the endogenous receptor. The assumption was tested by expressing both rat and chicken trkA receptors in the same cell and activating them with either neurotrophic growth factor (NGF), which binds both receptors, or with the CTA antibody, which binds only the chick receptor. While the chick receptor became phosphorylated by both treatments, activation of the rat receptor was detected only after NGF addition. Thus, the activated chick receptor did not in turn activate the rat receptor. The effects of the CTA antibody preparation were therefore not attributable to activation of endogenous trkA receptors.

The sympathetic and sensory neurons used in the experiments were cultured in a defined medium. Hawrot and Patterson, 1979, *Methods Enzymol.* 53: 574–584. Sympathetic neurons were isolated from superior cervical ganglia dissected from E20–E21 rat fetuses, while dorsal root ganglion sensory neurons were obtained from E16–E18 rats. The ganglia were treated with 0.25% trypsin for 10 minutes, washed, and triturated to obtain lab a single cell suspension. Sensory neurons were preplated for 1 hour on tissue culture plastic to deplete adherent cells. Sensory and sympathetic neurons were infected with adenoviruses directing expression of RPTKs that comprise the chicken extracellular domain for two hours on collagen I-coated tissue culture plastic in the presence of NGF. The cells were then washed and allowed to recover for two to four additional hours in the presence of NGF. After the recovery period, the cells were washed extensively to remove the growth factor, and plated onto polylysine-laminin coated chamber slides with 15 $\mu$g/mL RTA or CTA IgG, or no addition. After an additional two days (sensory) or three days (sympathetic), the cultures were stained with calcein AM (1 $\mu$g/mL) for 45 minutes, mounted and examined by immunofluorescence. Generally, five disperse fields representing 7% of the well were photographed and the number of surviving neurons quantified.

The conditions for immunoprecipitation and immunoblotting used in the experiments were described previously (Clary et al., 1994, *Mol. Biol. Cell* 5: 549–563) with modifications as follows. Immunoblots were performed in Tris-buffered saline containing 0.1% Triton X-100, and filter blocking and antibody incubations were performed in the same buffer with 1% BSA. In other experiments, anti-phosphotyrosine detection was performed with biotinylated-4G10 monoclonal antibody followed by a peroxidase avidin-biotin complex. Other antibodies were detected with peroxidase coupled anti-mouse IgG, anti-rabbit IgG, or protein A as indicated. All peroxidase conjugates were detected using a chemiluminescence protocol (Pierce Chemical Co. Rockford, Ill.).

Example 5

Construction of Adenoviral Vectors Expressing Receptor Constructs

In order to test the biochemical effect of receptor tyrosine kinases in chimeric receptor constructs, a method for efficient gene transfer was developed which would work with multiple cell lines as well as primary neuronal cultures. A recombinant adenoviral system was developed, as adenovirus exhibits a wide host range, and can infect and direct gene expression in post-mitotic neurons.

Recombinant adenoviruses were generated by in vivo ligation. The transfer vector (pAdRSVOES-) contained a 5' adenovirus packaging sequences, the Rous Sarcoma Virus long terminal repeat promoter, a polylinker ending in the restriction site BstBI, the SV40 poly A region, 31 adenoviral sequences (which could be used for recombination), and sequences for propagation in E. coli. The viral DNA used for generation of recombinant viruses was derived from a virus which expressed the β-galactosidase gene driven by the RSV promoter, and which contained a BstBI site between the β-galactosidase gene and the poly A region. This vector allowed screening for recombinant plaques based on the presence or absence of β-galactosidase activity, similar to a system described by Schaack and colleagues. Schaack et al., 1995, *J. Virol.* 69: 3920–3923. This virus lacks the E3 region.

The cells utilized for the generation of recombinant adenovirus were HEK293 cells. Early passage HEK293 cells (Graham et al., 1977, *J. Gen. Virol* 36: 59–72) were maintained in Dulbecco's modified Eagles medium+10% calf serum. Cells infected with recombinant adenovirus were detected as plaques in the cell monolayer. Typically, 5 $\mu$g of transfer vector plasmid DNA cleaved by digestion with BstBI were coprecipitated with 2 $\mu$g of viral DNA also cleaved with BstRI. HEK293 monolayers were transfected with the DNA and cultured from five to seven days to allow plaques to appear. The monolayers were then stained with 25 $\mu$g/mL X-GAL (5-bromo-4-chloro-3-indolyl-β-D-galactopyranoside) for several hours to identify non-recombinant (stained) plaques. Putative recombinant plaques were screened for expression of the transgene by infection of HEK293 cultures followed by immunohistochemistry. Viruses which were positive for transgene protein expression were picked and subjected to several rounds of plaque purification prior to amplification and purification on cesium chloride gradients. Banded viruses were diluted five-fold with dilution buffer (Curiel et al., 1991, *Proc. Natl. Acad. Sci. USA* 88: 8850–8854) and stored at −80° C. Approximate titers of the virus preparations were determined immunohistochemically on HEK293 cultures. Although recombinant viruses were generated through recombination into the viral genome or through cotransfection of cleaved DNAs, higher recovery of recombinants was achieved through the cleaved DNA method. The putative recombinant viruses were screened for expression of the kinase transgene by immuno-histochemistry.

Immuno-histochemistry techniques were performed on cultures of sympathetic neurons infected with the RSV KP or RSV c-ret viruses and fixed and stained as described. Lefcort et al., 1996, *J. Neurosci.* 16: 3704–3713. The primary antibodies were the CTA IgG, and mouse anti-tyrosine hydroxylase. The primaries were detected with Cy3-anti rabbit IgG and fluorescein-anti mouse IgG.

Example 6

Expression and Activation of C-RET, SEK, and MCK-10 Chimeras

Once the adenoviral expression vectors were transfected into the neuronal cells, an initial survey of RPTK expression was performed for these cells. Several uncharacterized kinases were expressed in these cell types. For example, the RPTK sek was expressed in embryonic rat motor neurons, while MCK-10 (DDR) and c-ret were expressed in both motor and sympathetic neurons.

DNA constructs were generated, which encoded the transmembrane and cytoplasmic domains from human MCK-10, C-RET, mouse SEK, and rat TRKA fused to the chicken TRKA extracellular domain. These chimeric receptor constructs were then inserted into the adenovirus transfer vector, and recombinant viruses were generated and purified. Rat C6 glioma cells were infected with the recombinant viruses, and the resulting chimeric receptors were analyzed via immunoblot analysis.

The chimeric ret protein appeared to be approximately 155 kDa as expected. The chimeric sek protein was approximately 150 kDa, which is very similar to the chimeric and non-chimeric trkA constructs, which have a molecular weight of approximately 140 kDa, and consistent with a fully processed, mature receptor. The MCK-10 chimeric protein appeared in three bands, of molecular weights of approximately 160, 120, and 105 kDa. The two lower molecular weight forms were quite abundant and probably represent immature forms of this chimera.

Once it was determined that the chimeric receptors were expressed in the cells, their activity was determined by monitoring the degree that they autophosphorylation after stimulation by ligand, e.g. the trkA CTA antibody.

The ability to activate the chimeras was evaluated by incubating the infected C6 monolayers with 50 ng/mL NGF for five minutes. The receptors were immunoprecipitated with the CTA antibody, immunoblotted, and probed either with the anti-phosphotyrosine antibody 4G10 or with the CTA antibody preparation. NGF-dependent activation of the c-ret and sek chimeras was detected by the anti-phosphotyrosine antibody. The chimeric c-ret receptor showed a substantial activation in the absence of ligand addition. Phosphotyrosine was not detected for the MCK-10 chimeric protein, either before or after incubation with NGF.

The PC12 and C6 glioma cells used in the experiments were cultured as follows. PC12 cultures (Greene et al., 1987, *Methods Enzymol.* 147: 207–216) were maintained in RPMI medium containing 10% horse serum and 5% fetal calf serum. For differentiation experiments the medium was changed to RPMI containing IX N2 supplement and 0.1% BSA, and the cells were grown on a collagen I substrate. For PC12 cell survival, the cells were grown in RPMI containing 0.1% BSA. All cultures also contained IX penicillin/streptomycin. For adenoviral infections, PC12 cells were incubated overnight with recombinant viruses at a multiplicity of infection (MOI) between 1 and 10. The cells were then washed and replated either into differentiation or survival conditions, with either no addition or addition of 50 ng/mL (NGF) or 20 $\mu$g/mL CTA IgG for two days.

For differentiation experiments, the cell cultures were fixed with 2% paraformaldehyde and the percentage of cells bearing processes longer than 1 cell diameter was determined. For survival, the cultures were incubated with 0.05% MTT for 1.5 hours to stain living cells, and the relative number of cells surviving in each condition was determined.

C6 glioma cells were grown in Ham's Flo medium containing 10% fetal calf serum; for receptor activation experiments the medium was changed to 0.5% fetal calf serum 12 hours prior to stimulation.

Example 7

The C-RET Chimeric Receptor Promotes Differentiation and Survival of PC12 Cells

The biological activities of the chimeric receptor constructs were tested after it was determined that these constructs were expressed and active when stimulated with the CTA antibody, as shown in example 6. As a first test of the biological activities of these chimeric constructs, their effects on the differentiation and serum-free survival of the pheochromocytoma cell line PC12 were tested.

Lysates from PC12 cultures prepared two days after infection with viruses were probed for receptor expression with the CTA antibody. Strong expression of the full length and chimeric trkA and MCK-10 receptors was observed. Lower levels of the c-ret and sek receptors were expressed. As expected, the CTA antibody did not react with uninfected cultures or cultures infected with the β-galactosidase virus.

To examine the effects of these receptors on cell differentiation, the PC12 cells were first treated with virus overnight, and then replated under conditions which promote cellular differentiation. The cultures were incubated either in the presence of CTA IgG, to activate the introduced receptors, or NGF, to activate both endogenous and exogenous pools. The CTA antibody preparation could promote extensive outgrowth of the PC12 cells infected with the c-ret chimeric virus as well as with the full length and chimeric trkA viruses. The antibody had no obvious effect on RSV sek or RSV MCK-10.

The percentage of cells undergoing differentiation was quantified in each condition. RSV c-ret was able to promote differentiation of PC12 cells to a level comparable to that seen with either trkA construct. RSV c-ret virus showed a much higher activity in the absence of ligand than the trkA viruses did, most likely due to its auto-activation. No detectable activity of the sek or MCK-10 constructs was observed.

The effects of the viruses on PC12 cell death was also tested. PC12 cells undergo programmed cell death in the absence of serum, and can be rescued by NGF. PC12 cells infected with the recombinant adenoviruses were tested for the ability of CTA antibody to rescue these cells from serum deprivation. The cells were infected as described above, and plated with and without CTA Antibody in serum free medium. MTT was used to detect surviving cells in the cultures two days later. The strongest effect on cell survival was observed for the two trkA receptor constructs. The c-ret chimeric receptor could prevent cell death as well, but its effect reached a plateau at a level below that of the trkA viruses. The RSV sek and RSV MCK-10 viruses had marginal if any effect on the rescue of cells from death.

Hence, the c-ret cytoplasmic domain had biological activities comparable to those of trkA in promoting PC12 cell differentiation and PC12 cell survival, while these activities were not detected after transfection with the sek or MCK-10 receptor chimeras.

Example 8

Activation of the C-RET Chimera Promotes Survival of Embryonic Sympathetic Neurons C-ret was activated in a ligand-independent manner and tested for its ability to prevent apoptosis in embryonic sympathetic neurons. Sympathetic neurons extend processes and maintain viability and electrical excitability for weeks when cultured in the presence of NGF. In the absence of NGF, the neurons lose their processes, shrivel and undergo a classical program of apoptosis within hours. Activation of the trkA receptor can prevent apoptosis in sympathetic neurons without the addition of NGF.

The expression of chimeric receptor constructs was examined in rat sympathetic neurons by infecting the neurons, culturing them in the presence of RTA antibody, and lysing them 48 hours later. The RTA antibody was used to maintain their viability in the event that expression of a trkA chimera would inhibit the function of the endogenous rat trkA when NGF was used as a ligand. The lysates were immunoblotted and probed with the CTA antibody. Strong expression of RSV KP (trkA chimera), RSV c-ret, and RSV sek was observed. RSV MCK-10 showed somewhat weaker expression, especially of the 160 kDa isoform.

The neurons were transfected and plated in order to examine the effects of the chimeric receptors on neuronal cell survival. The infected neurons were cultured in the presence of RTA antibody to activate their endogenous trkA receptor, CTA antibody to activate the introduced receptor, or no addition to examine the background of cell survival. After three days, the cultures were stained with the vital dye calcein AM, and the number of surviving neurons in each condition was determined.

Uninfected sympathetic neurons responded well to the RTA antibody preparation, while the CTA antibody was ineffective in promoting cell survival. RTA could also sustain the survival of neurons infected with the RSV KP, RSV c-ret, RSV sek, or RSV MCK-10 viruses. Moreover, infection of the neurons with RSV KP (the chimeric trkA virus) resulted in the ability of the neurons to respond to CTA, and the level of survival measured in the presence of CTA reached levels equal to the survival promoted by RTA antibody. This indicated that survival of primary neurons could be promoted by introduction and activation of RPTKs.

Increased survival of sympathetic neurons was also observed when they were infected with the RSV c-ret virus and cultured with the activating CTA antibody. The level of survival reached approximately 50% of the maximal level attained with the RSV KP virus. In addition, a substantial increase in survival in the absence of the activating antibody was measured. About 30% of the neurons survived compared to RSV KP plus the activating antibody. This result was not unexpected, given the relatively high level of autoactivation detected with this chimeric receptor. Even though there was significant survival in the RSV KP wells in the absence of CTA antibody, it was not as striking as with RSV c-ret. Finally, neither the RSV sek nor the RSV MCK-10 virus could increase the survival of the neurons in the presence of CTA antibody, in contrast to the survival seen with RSV KP and RSV c-ret.

The cells surviving through infection with the RSV c-ret virus were tested for the proper phenotype of a superior cervical ganglion neuron. Neurons were cultured with or without NGF for two days following infection with either the RSV c-ret or the RSV KP virus. The cultures were then subjected to immunofluorescence. In all cases neurons which were strongly expressing the chimeric receptors exhibited a healthy phenotype. When the cultures were supplemented with NGF, the cells expressing the transgene comprised a subset of surviving neurons, while in the absence of NGF, all large healthy neurons were found to be expressing the chimeric receptor. In addition, the neurons expressed comparable levels of tyrosine hydroxylase as compared to RSV KP controls. In cultures sustained by infection with the RSV c-ret virus only, the levels of tyrosine hydroxylase appeared to be highest in the cells expressing the highest levels of chimeric receptor, indicating that c-ret may be acting like the trsu receptor in upregulating tyrosine hydroxylase in activity.

Example 9

Prevention of Sensory Neuron Programmed Cell Death by the C-RET Intracellular Region C-ret constructs were transfected into DRG embryonic rat sensory neurons to determine whether the RPTK could promote survival in these cells as well as the sympathetic neurons studied in example 5.

All three of the receptors were robustly expressed in the DRG neuronal cell cultures. After plating the cells, both the trkA and c-ret chimeric receptors could promote a significant level of neuronal survival, while the sek receptor construct was inactive. The level of survival promoted by c-ret in the presence of the CTA antibody was about 50% of that promoted by RSV KP, and again there was significant survival in the absence of the antibody (31% of that measured with RSV KP plus CTA antibody). Therefore, the survival activity of the c-ret receptor intracellular region extends to at least two major cell types, sympathetic and sensory neurons, in the peripheral nervous system.

Example 10

TRKA and C-RET Chimeric Receptors Promote MAPK Phosphorylation in Primary Neurons The molecular mechanisms behind cell survival were explored once it was observed that activation of the c-ret chimera stimulated cell survival, as demonstrated in examples 5 and 6. In particular, the relationship between the c-ret intracellular region and the proteins that it potentially phosphorylated were explored.

Analysis of downstream signal transduction effectors of the trkA and c-ret receptors showed significant similarities in certain effector systems. For example, GRB2 has been shown to bind one isoform of the c-ret receptor at its cytoplasmic tail; this interaction is predicted to activate the ras/raf/MAPK pathway. TrkA activates this pathway through interaction of the SHC adaptor protein with a phosphotyrosine located in the juxtamembrane region. Experiments were performed which determined that survival-promoting receptors could activate the MAPK pathway in sympathetic neurons.

Neurons were infected with virus constructs carrying either active or inactive trkA receptor genes or the chimeric c-ret receptor gene. The neurons were cultured in the presence of the RTA antibody for two days, and then starved for 3 hours. Half of the wells were stimulated for ten minutes with the CTA antibody, the cultures were lysed, and the resulting lysates immunoblotted. The immunoblots were probed with antibodies recognizing MAPK p42 and p44 (ERK1 and ERK2) or probed with antibodies recognizing only the phosphorylated form of MAPK.

CTA stimulation of the RSV KP and RSV c-ret receptors efficiently and equivalently promoted MAPK phosphorylation. In addition, significant phosphorylation of MAPK with RSV c-ret was observed in the absence of stimulation, consistent with the observation that this construct was autoactivated. Thus, the correlation between the roles of trkA and c-ret in promoting primary neuronal survival and activating the MAPK pathway suggest that the MAPK pathway is a component of the apoptosis mechanism.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed.

In particular, although some formulations described herein have been identified by the excipients added to the formulations, the invention is meant to also cover the final formulation formed by the combination of these excipients. Specifically, the invention includes formulations in which one to all of the added excipients undergo a reaction during formulation and are no longer present in the final formulation, or are present in modified forms.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are within the following claims.

What is claimed is:

1. A method of preventing or treating a neurodegenerative disorder in a mammal, wherein said neurodegenerative disorder is caused by an aberration in cell survival, said method comprising the step of administering a pharmaceutical composition comprising one or more compounds to said mammal, wherein said compound is a modulator of a C-RET receptor protein tyrosine kinase, and wherein said compound is an indolinone compound of Formula I:

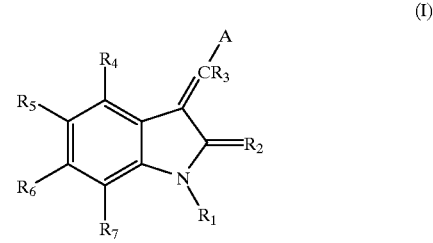

(I)

wherein,
R$_1$ is hydrogen or alkyl;
R$_2$ is oxygen or sulfur;
R$_3$ is hydrogen;
R$_4$, R$_5$, R$_6$, and R$_7$ are each independently selected from the group consisting of hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R, CONRR', and (CH$_2$)$_n$ONRR';
A is a five-membered heteroaryl ring selected from the group consisting of thiophene, pyrrole, pyrazole, imidazole, 1,2,3-triazole, 1,2,4-triazole, oxazole, isoxazole, thiazole, isothiazole, 2-sulfonylfuran, 4-alkylfuran, 1,2,3-oxadiazole, 1,2,4-oxadiazole, 1,2,5-oxadiazole, 1,3,4-oxadiazole, 1,2,3,4,-oxatriazole, 1,2,3,5-oxatriazole, 1,2,3-thiadiazole, 1,2,4-thiadiazole, 1,2,5-thiadiazole, 1,3,4-thiadaizole, 1,2,3,4-thiatriazole, 1,2,3,5-thiatriazole, and tetrazole, wherein said five-membered ring is optionally substituted at one or more positions with one or more substituents independently selected from the group consisting of alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R, CONRR', and (CH$_2$)$_n$ONRR';

n is 0–3;

R is selected from the group consisting of hydrogen, alkyl, and aryl; and

R' is selected from the group consisting of hydrogen, alkyl, and aryl, wherein said alkyl is optionally substituted with a six-membered heteroaliphatic ring, and wherein said six-membered ring is optionally substituted at one or more positions with substituents selected from the group consisting of alkyl, alkoxy, halogen, trihalomethyl, NO$_2$, and (CH$_2$)$_n$CO$_2$R.

2. The method of claim 1, wherein said method prevents or reduces a symptom associated with said neurodegenerative disorder.

3. The method of claim 2, wherein said neurodegerative disorder is selected from the group consisting of Alzheimer's disease, Parkinson's disease, and amyotrophic lateral sclerosis.

4. The method of claim 1, wherein said one or more compounds are identified by a method comprising:

(a) expressing said C-RET in cells;

(b) contacting said cells with one or more compounds; and (c) monitoring an effect on said cells.

5. The method of claim 4, wherein said effect is a change or an absence of a change in cell phenotype.

6. The method of claim 4, wherein said effect is a change or an absence of a change in catalytic activity of said C-RET.

7. The method of claim 4, wherein said effect is a change or an absence of a change in the interaction between said C-RET and a natural binding partner.

8. The method of claim 1, wherein said A is selected from the group consisting of thiophene and pyrrole, wherein said thiophene and pyrrole are optionally substituted with one or more substituents selected from the group consisting of alkyl, alkoxy, aryl, aryloxy, alkaryl, alkaryloxy, halogen, trihalomethyl, S(O)R, SO$_2$NRR', SO$_3$R, SR, NO$_2$, NRR', OH CN, C(O)R, OC(O)R, NHC(O)R, (CH$_2$)$_n$CO$_2$R, CONRR', and (CH$_2$)$_n$ONRR;

n is 0–3;

R is selected from the group consisting of hydrogen, alkyl, and aryl; and

R' is selected from the group consisting of hydrogen, alkyl, and aryl, wherein said alkyl is optionally substituted with a six-membered heteroaliphatic ring, and wherein said six-membered ring is optionally substituted at one or more positions with substituents selected from the group consisting of alkyl, alkoxy, halogen, trihalomethyl, NO$_2$, and (CH$_2$)$_n$CO$_2$R.

9. The method of claim 1, wherein said one or more compounds are selected from the group consisting of

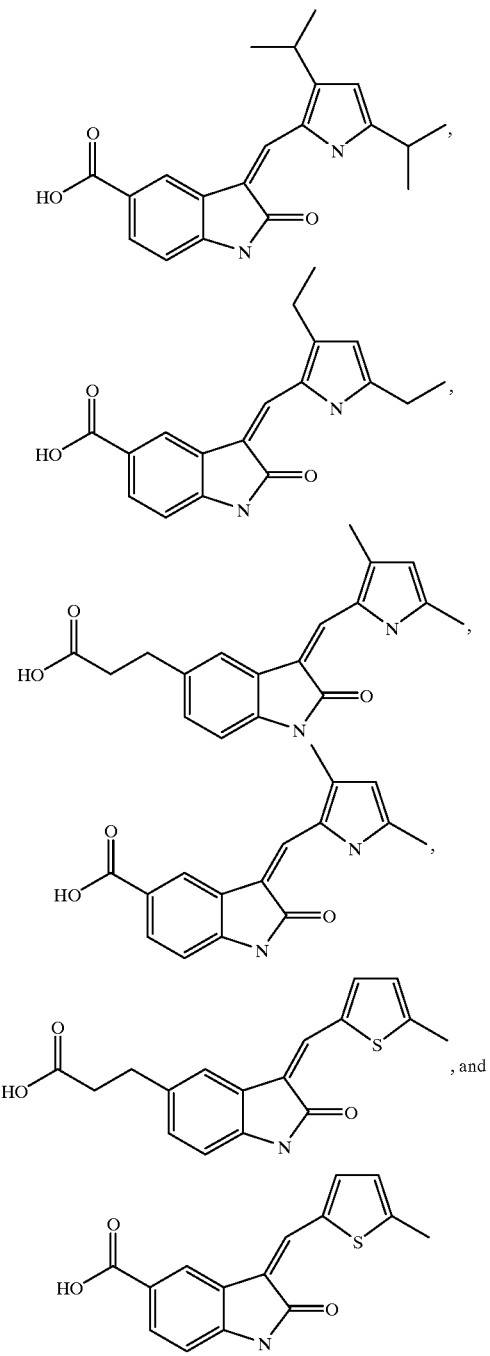

10. The method of claim 1, wherein said one or more compounds is a non-peptide molecule.

11. The method of claim 1, wherein said one or more compounds act intracellularly.

12. The method of claim 1, wherein said one or more compounds can traverse the blood-brain barrier.

13. The method of claim 1, wherein said pharmaceutical composition further comprises one or more physiologically acceptable solvents in a formulation.

14. The method of claim 13, wherein said formulation is selected from the group consisting of a parenteral, an oral, and a topical formulation.

* * * * *